Figure 1:
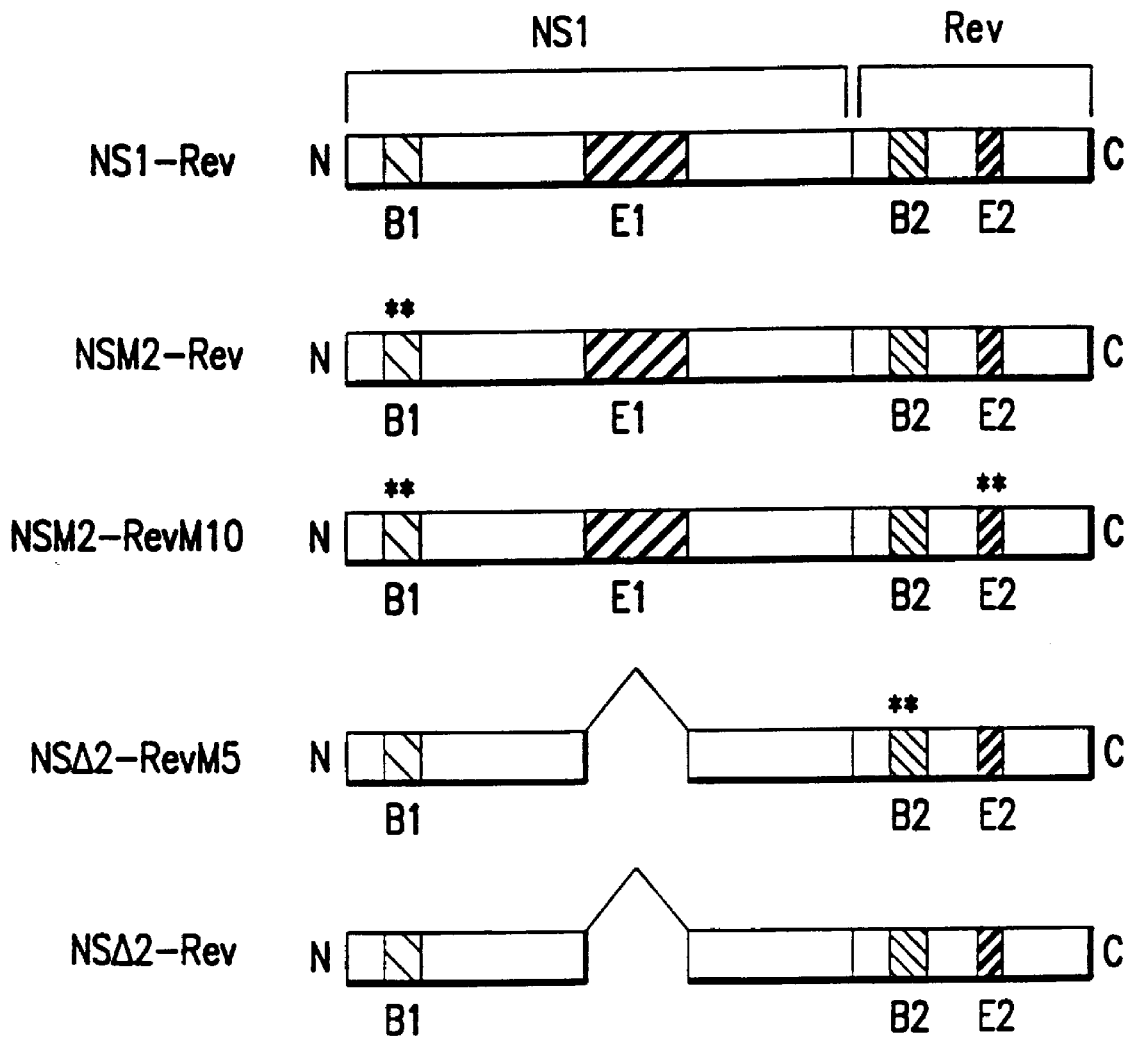

United States Patent [19]
Krug et al.

[11] Patent Number: 5,843,724
[45] Date of Patent: Dec. 1, 1998

[54] CHIMERIC NUCLEIC ACIDS AND PROTEINS FOR INHIBITING HIV-1 EXPRESSION

[75] Inventors: Robert M. Krug, Princeton; Xiao Yan Qian, Highland Park, both of N.J.

[73] Assignee: Rutgers University, Piscataway, N.J.

[21] Appl. No.: 467,587

[22] Filed: Jun. 6, 1995

Related U.S. Application Data

[63] Continuation-in-part of Ser. No. 429,761, Apr. 27, 1995, abandoned.
[51] Int. Cl.$^6$ .......................... C07K 14/00; C12N 15/40; C12N 15/63; C12N 5/10
[52] U.S. Cl. .................. 435/69.7; 530/350; 536/23.4; 435/252.3; 435/320.1; 435/372.3
[58] Field of Search .............................. 435/69.1, 69.7, 435/252.3, 320.1, 372.3; 514/2, 44; 530/350; 536/23.1, 23.4, 23.72

[56] References Cited

U.S. PATENT DOCUMENTS 5,174,993  12/1992  Paolette ............................... 424/199.1

OTHER PUBLICATIONS

Johnston et al. (May 1993) Present status and future prospects for HIV therapies. Science 260:1286–1293.
Fox (Feb. 1994) No winners against AIDS. Bio/Technology 12:128.
Orkin et al. (Dec. 1995) Report and recommendations of the panel to assess the NIH investment in research on gene therapy.
Qian (Apr. 1995) Dissertation Abstracts International 56/06–B:3045.
Irene Weichselbraun, et al., "Definition of the Human Immunodeficiency Virus Type 1 Rev and Human T–Cell Leukemia Virus Type 1 Rex Protein Activation Domain by Functional Exchange", Journal of Virology, Apr. 1992, pp. 2583–2587.
Bevec, Dorian, et al. , "Inhibition of human immunodeficiency virus type 1 replication in human T cells by retroviral–mediated gene transfer of a dominant–negative Rev trans–activator", Biochemistry, Proc. Natl. Acad. Sci., USA, vol. 89, pp. 9870–9874, Oct. 1992.
Zapp, Maria L., et al. "Oligomerization and RNA binding domains of the type 1 human immunodeficiency virus Rev protein: A duel function for an arginine–rich binding motif", Biochemistry, Proc. Natl. Acad. Sci USA, vol. 88, pp. 7734–7738, Sep. 1991.
Felber, Barbara K., et al. "Rev protein of human immunodeficiency versus type 1 affects the stability and transport of the viral MRNA", Biochemistry, Proc. Natl. Acad. Sci. USA, vol. 86, pp. 1495–1499, Mar. 1989.
Madore, Steven J., et al., "Sequence Requirements for Rev Multimerization In Vivo", Virology vol. 202, pp. 186–194, 1994.

Hadzopoulou–Cladaras, Margarita, et al., "The rev(trs/art) Protein of Human Immunodeficiency Virus Type 1 Affects Viral mRNA and Protein Expression via cis–Acting Sequence in the env Region", Journal of Virology, pp. 1265–1274, Mar. 1989.
Malim, Michael H., et al., "HIV–1 Structural Gene Expression Requires the Binding of Multiple Rev Monomers to the Viral RRE: Implications for HIV–1 Latency", Cell, vol. 65, pp. 241–248, Apr. 19, 1991.
Fortes, Purificacion, et al., "Influenza virus NS1 protein inhibits pre–mRNA splicing and blocks mRNA nucleocytoplasmic transport", The EMBO Journal, vol. 13, No. 3., pp. 704–712, 1994.
Mermer, Brion, et al., "Identification of trans–dominant HIV–1 rev protein mutants by direct transfer of bacterially produced proteins into human cells", Nucleic Acids Research, vol. 18, No. 8, pp. 2037–2044, 1990.
Malim, Michael H., "Stable Expression of Transdominant Rev Protein in Human T Cells Inhibits Human Immunodeficiency Virus Replication", J. Exp. Med., vol. 176, pp. 1197–1201, Oct. 1992.
Olsen, Henrik S., et al., "Interaction of the human immunodeficiency virus type 1 Rev protein with a structured region in env MRNA is dependent on multimer formation mediated through a basic stretch of amino acids", Genes & Development, pp. 1357–1364, 1990.
Bogerd, Hal, et al. "Dominant Negative Mutants of Human T–Cell Leukemia Virus Type 1 Rex and Human Immunodeficiency Virus Type 1 Rev Fail to Multimerize In Vivo", Journal of Virology, pp. 2496–2502, May 1993.
Alonso–Caplen et al., 1992, Nucleocytoplasmic transport: the influenza virus NS1 protein regulates the transport of spliced NS2 mRNA and its precursor NS1 mRNA, Genes & Development 6:255–267).
Baltimore, 1988, Intracellular immunization, Nature 335:395–396.
Berchtold et al., 1994, Exchange of Functional Domains between Rev Proteins of HIV–1 and SIVmac239 Results in a Dominant Negative Phenotype, Virology 204:436–41.
Benoist and Chambon, 1981, In vivo sequence requirements of the SV40 early promoter region, Nature vol. 290:304–310.
Brinster et al., 1982, Regulation of metallothionein–thymidine kinase fusion plasmids injected into mouse eggs, Nature vol. 296:39–42.
Ceccoli, J. et al., 1989, Encapsulation of the UV–DNA Repair Enzyme T4 Endonuclease V in Liposomes and Delivery to Human Cells, The Society for Investigative Dermatology, Inc. vol. 93:190–194.

(List continued on next page.)

Primary Examiner—George C. Elliott
Assistant Examiner—Robert Schwartzman
Attorney, Agent, or Firm—Davidson, Davidson & Kappel, LLC

[57] ABSTRACT

A chimeric nucleic acid molecule encoding an NS1-Rev fusion protein having Rev function inhibitory activity.

36 Claims, 11 Drawing Sheets

OTHER PUBLICATIONS

Chaudhary et al., 1989, A recombinant immunotoxin consisting of two antibody variable domains fused to Pseudomonas exotoxin, *Nature* 339:394–397.

Chomczynski et al., 1987, Single–Step Method of RNA Isolation by Acid Guanidinium Thiocyanate–Phenol–Chloroform Extraction, *Analytical Biochemistry*, 162:156–159.

Cullen, 1994, Infectious Agents & Disease 3(2–3):68–76.

Feinberg et al., 1986, HTLV–III Expression and Production Involve Complex Regulation at the Levels of Splicing and Translation of Viral RNA, *Cell*: vol. 46; 807–817.

Gunning, et al., 1987, A human β–actin expression vector system directs high–level accumulation of antisense transcripts, *Proc. Natl. Acad. Sci. USA,* 84:4831–4835.

Hamm et al., 1990, Monomethylated Cap Structures Facilitate RNA Export from the Nucleus, *Cell,* vol. 63:109–118.

Hope et al., 1992, trans–Dominant Inhibition of Human Immunodeficiency Virus Type 1 Rev Occurs through Formation of Inactive Protein Complexes, *Journal of Virology,* vol. 66:1849–1855.

Huston et al., Protein Engineering of Single–Chain Fv Analogs and Fusion Proteins, *Molecular Design and Modeling: Concepts and Applications,* Part B, ed. J.J. Langone, *Methods in Enzymology* 203:46–88.

Karasuyama, H., et al., 1989, Autocrine Growth and Tumorigenicity of Interleukin 2–Dependent Helper T Cells Transfected with IL–2 Gene, *J. Exp. Med, The Rockefeller University Press.,* vol. 169:13–25.

Klessig, D.F., et al., 1984, Introduction, Stable Integration, and Controlled Expression of a Chimeric Adenovirus Gene Whose Product Is Toxic to the Recipient Human Cell, *Mol.ecular and Cellular Biology.,* vol. 4:1354–1362.

Lamb et al, 1980, Sequence of Interrupted and Uninterrupted mRAs and Cloned DNA Coding for the Two Overlapping Nonstructural Proteins of Influenza Virus, *Cell* 21:475–485.

Levy et al., 1992, Viral and Immunologic Factors in HIV Infection, *The Medical Management of AIDS*, Third Edition, Eds, Sandy et al., W.B. Saunders Company.

Lu et al., 1994, "The influenza virus NS1 protein: a novel inhibitor of pre–mRNA Splicing." *Genes and Development* 8:1817–1828.

Malim et al., 1989, Functional Dissection of the HIV–1 Rev Trans–Activator–Derivation of a Trans–Dominant Repressor of Rev Function, *Cell* vol. 58:205–214.

Malim et al., 1989, The HIV–1 *rev trans*–activator acts through a structured target sequence to activate nuclear export of unspliced viral mRNA, *Nature,* 338:254–257.

Malim et al., 1991, Mutational Definition of the Human Immunodeficiency Virus Type 1 Rev Activation Domain, *Journal of Virology* vol. 65:4248–4254.

Sambrook, J., et al., 1989: *Molecular Cloning (A Laboratory Manual)*, Cold Spring Harbor Laboratory, Cold Spring Harbor, New York.

Mannino, R.J. et al., 1988, Liposome Mediated Gene Transfer, *Biotechniques,* vol. 6 No. 7:682–690.

Meyer et al., 1994, The HIV–1 Rev Trans–activator shuttles between the nucleus and the cytoplasm, *Genes & Development,* 8(13):1538–47.

Newton, A.C. and Huestis, W.H., 1988, Vesicle–to–Cell Protein Transfer: Insertion of Band 3, the Erythrocyte Anion Transporter, into Lymphoid Cells, *Biochemistry,* 27:4655–4659.

Qian et al., 1994, Two Functional Domains of the Influenza Virus NS1 Protein Are Required for Regulation of Nuclear Export of mRNA, *Journal of Virology,* 68(4):2433–2441.

Qiu Y. and Krug RM, 1994, The Influenza Virus NS1 Protein Is a Poly(A)–Binding Protein That Inhibits Nuclear Export of mRNAs Containing Poly(A), *Journal of Virology,* 68(4):2425–32.

Ratner et al., 1987, Complete Nucleotide Sequences of Functional Clones of the AIDS Virus, *AIDS Research and Human Retroviruses,* vol. 3:57–69.

Sadaie et al., 1984, Site–Directed Mutagenesis of Two–Trans–Regulatory Genes (tat–III, trs) of HIV–1, *Science,* vol. 239:910–914.

Shaw et al., 1987, Molecular Characterization of Human T–Cell Leukemia (Lymphotropic) Virus Type III in the Acquired Immune Deficiency Syndrome, *Science* vol. 226:1165–1171.

Sodroski et al., 1986, A second post–transcriptional trans–activator gene required for HTLV–III replication, *Nature* vol. 321:412–417.

Tanswell, A.K. et al., 1990, Response of fetal rat lung fibroblasts to elevated oxygen concentrations after liposome–mediated augmentation of antioxidant enzymes, *Biochimica et Biophysica Acta,* 1044:269–274.

Terwilliger et al., The art Gene Product of Human Immunodeficiency Virus Is Required for Replication, *Journal of Virology,* vol. 62:655–658, 1988.

Tiley et al., 1991, Conserved Functional Organization of the Human Immunodeficiency Virus Type 1 and Visna Rev Proteins, *Journal of Virology* vol. 65:3877–3881.

Wagner et al., 1981, Nucleotide sequence of the thymidine kinase gene of herpes simplex virus type 1, *Proc. Natl.Acad. Sci. U.S.A.* 78:1441–1445.

Weiss, R., et al., 1985 *RNA Tumor Viruses,* Cold Spring Harbor Laboratory, Cold Spring Harbor, New York.

Wolfe, J.H., et al., 1992, Herpesvirus vector gene transfer and expression of β–glucuronidase in the central nervois system of MPS VII mice, *Nature Genetics,* vol. 1:379–384.

Yamada et al., 1985, Overproduction of the protein product of a nonselected foreign gene carried by an adenovirus vector, *Proc. Natl. Acad. Sci.* U.S.A. vol. 82(11):3567–71.

Yamamoto et al., 1980, Identification of a Functional Promoter in the Long Terminal Repeat of Rocus Sarcoma Virus, *Cell* vol. 22:787–797.

```
                67                                                92
cRev         S  A  E  P  V  P  L  Q  L  P  P  L  E  R  L  T  L  D  C  N  E  D  C  G  T  S
                                                                                              ACTIVITY
MUTANT                                                                                          p24
                                                                                           gTAT (% OF WT)
M9              D  L                                                                        ++      90
M10                            D  L                                                          -      <1
M11                                                          D  L                           ++     100
M15          D  L                                                                           ++      70
M16             D  L                                                                        ++      65
M17                D  L                                                                     ++      65
M18                   D  L                                                                   +      30
M19                      D                                                                  ++      60
M20                         D  L                                                            ++      50
M21                            D  L                                                          -      <1
M22                               D  L                                                       -      <1
M23                                  E  D  L                                                ++      70
M24                                     K  D  L                                             ++      50
M25                                        E  D  L                                          ++      70
M27                         A                                                                -      <1
M28                            A                                                             -      <1
M29                               A                                                          -      <1
M32                         A  A  A                                                          -      <1
M33                                        N  S                                             ++      80
M34                                           V                                             ++      75
M35                                  Q                                                      ++      60
M36                                  V                                                       +      15
Δ9/19        D -- -- -- -- -- -- --                                                          -      <1
Δ18/19                         D -- --                                                       +      20
Δ18/23                         D -- -- -- -- -- -- -- -- -- L                                -      <1
Δ22/14                                     D -- -- -- -- -- -- -- -- -- -- -- -->            -      <1
Δ23/14                                        E -- -- -- -- -- -- -- -- -- -- -->           ++      30
```

FIG. 9A

NLS1
                                                                ‾‾‾‾
1    MDSNTV SSFQ   VDCFLWHV RK   QVVDQELGDA   PF LD RL RR DQ
             ‾‾                  ‾‾           ‾‾    ‾‾ ‾‾ ‾‾
              1           2                    3    4  5

41   KSLRGRG STL   GLNIEAATHV   G KQ IVEKILK   EE SD EALKMT
             ‾‾‾              ‾‾‾              ‾‾
              6                 7              8

81   MASTPA SR YI   TDMTIEEL SR   DWFMLMPKQK   VEGPL C IRID
             ‾‾              ‾‾                      ‾
              9              10                      11

121  QAIMDKNIML   KAN FSV IFDR   LETLILLRA F    T EEGAIVGE I
                     ‾‾‾                 ‾‾    ‾‾         ‾‾
                      12                  13              14

161   S PLPSFPGHT   IEDV KN AIGV   LIGGLEWNDN   TVRVSKTL QR
     ‾‾                  ‾‾                             ‾‾
      15                  15                             16

201  FAWG SS NENG   RPPLTPKQ KR    K MARTARSKV   RRDKMAD
          ‾‾              ‾‾    ‾‾
           17             18
                         ‾‾‾‾
                         NLS2

FIG.9B

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: unknown ( x i ) SEQUENCE DESCRIPTION: SEQ ID NO:1:

```
TTAGGCATCT CCTATG                                                    16
```

( 2 ) INFORMATION FOR SEQ ID NO:2:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: unknown ( x i ) SEQUENCE DESCRIPTION: SEQ ID NO:2:

```
TGTTCGAACT CCTATG                                                    16
```

( 2 ) INFORMATION FOR SEQ ID NO:3:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: unknown ( x i ) SEQUENCE DESCRIPTION: SEQ ID NO:3:

```
GTTCGAACTC CTATG                                                     15
```

( 2 ) INFORMATION FOR SEQ ID NO:4:

( i ) SEQUENCE CHARACTERISTICS:
        ( A ) LENGTH: 237 amino acids
        ( B ) TYPE: amino acid
        ( D ) TOPOLOGY: LINEAR ( x i ) SEQUENCE DESCRIPTION: SEQ ID NO: 4:

```
Met Asp Ser Asn Thr Val Ser Ser Phe Gln Val Asp Cys Phe Leu Trp
 1               5                  10                  15
His Val Arg Lys Gln Val Val Asp Gln Glu Leu Gly Asp Ala Pro Phe
                20                  25                  30
Leu Asp Arg Leu Arg Arg Asp Gln Lys Ser Leu Arg Gly Arg Gly Ser
                35                  40                  45
Thr Leu Gly Leu Asn Ile Glu Ala Ala Thr His Val Gly Lys Gln Ile
 50                  55                  60
Val Glu Lys Ile Leu Lys Glu Glu Ser Asp Glu Ala Leu Lys Met Thr
 65                  70                  75                  80
Met Ala Ser Thr Pro Ala Ser Arg Tyr Ile Thr Asp Met Thr Ile Glu
                85                  90                  95
Glu Leu Ser Arg Asp Trp Phe Met Leu Met Pro Lys Gln Lys Val Glu
                100                 105                 110
Gly Pro Leu Cys Ile Arg Ile Asp Gln Ala Ile Met Asp Lys Asn Ile
                115                 120                 125
```

| Met | Leu | Lys | Ala | Asn | Phe | Ser | Val | Ile | Phe | Asp | Arg | Leu | Glu | Thr | Leu |
|---|---|---|---|---|---|---|---|---|---|---|---|---|---|---|---|
| | 130 | | | | 135 | | | | | 140 | | | | | |

| Ile | Leu | Leu | Arg | Ala | Phe | Thr | Glu | Glu | Gly | Ala | Ile | Val | Gly | Glu | Ile |
|---|---|---|---|---|---|---|---|---|---|---|---|---|---|---|---|
| 145 | | | | | 150 | | | | | 155 | | | | | |

| Ser | Pro | Leu | Pro | Ser | Phe | Pro | Gly | His | Thr | Ile | Glu | Asp | Val | Lys | Asn |
|---|---|---|---|---|---|---|---|---|---|---|---|---|---|---|---|
| | | | | 165 | | | | | 170 | | | | | 175 | |

| Ala | Ile | Gly | Val | Leu | Ile | Gly | Gly | Leu | Glu | Trp | Asn | Asp | Asn | Thr | Val |
|---|---|---|---|---|---|---|---|---|---|---|---|---|---|---|---|
| | | | 180 | | | | | 185 | | | | | 190 | | |

| Arg | Val | Ser | Lys | Thr | Leu | Gln | Arg | Phe | Ala | Trp | Gly | Ser | Ser | Asn | Glu |
|---|---|---|---|---|---|---|---|---|---|---|---|---|---|---|---|
| | | 195 | | | | | 200 | | | | | 205 | | | |

| Asn | Gly | Arg | Pro | Pro | Leu | Thr | Pro | Lys | Gln | Lys | Arg | Lys | Met | Ala | Arg |
|---|---|---|---|---|---|---|---|---|---|---|---|---|---|---|---|
| | 210 | | | | | 215 | | | | | 220 | | | | |

| Thr | Ala | Arg | Ser | Lys | Val | Arg | Arg | Asp | Lys | Met | Ala | Asp |
|---|---|---|---|---|---|---|---|---|---|---|---|---|
| 225 | | | | | 230 | | | | | 235 | | |

(2) INFORMATION FOR SEQ ID NO:5:

(i) SEQUENCE CHARACTERISTICS:
        (A) LENGTH: 26 amino acids
        (B) TYPE: amino acid
        (D) TOPOLOGY: LINEAR (xi) SEQUENCE DESCRIPTION: SEQ ID NO: 5:

| Ser | Ala | Glu | Pro | Val | Pro | Leu | Gln | Leu | Pro | Pro | Leu | Glu | Arg | Leu | Thr |
|---|---|---|---|---|---|---|---|---|---|---|---|---|---|---|---|
| 1 | | | | 5 | | | | | 10 | | | | | 15 | |

| Leu | Asp | Cys | Asn | Glu | Asp | Cys | Gly | Thr | Ser |
|---|---|---|---|---|---|---|---|---|---|
| | | | 20 | | | | | 25 | |

(2) INFORMATION FOR SEQ ID NO:6:

(i) SEQUENCE CHARACTERISTICS:
        (A) LENGTH: 26 amino acids
        (B) TYPE: amino acid
        (D) TOPOLOGY: LINEAR (xi) SEQUENCE DESCRIPTION: SEQ ID NO: 6:

| Asp | Leu | Glu | Pro | Val | Pro | Leu | Gln | Leu | Pro | Pro | Leu | Glu | Arg | Leu | Thr |
|---|---|---|---|---|---|---|---|---|---|---|---|---|---|---|---|
| 1 | | | | 5 | | | | | 10 | | | | | 15 | |

| Leu | Asp | Cys | Asn | Glu | Asp | Cys | Gly | Thr | Ser |
|---|---|---|---|---|---|---|---|---|---|
| | | | 20 | | | | | 25 | |

(2) INFORMATION FOR SEQ ID NO:7:

(i) SEQUENCE CHARACTERISTICS:
        (A) LENGTH: 26 amino acids
        (B) TYPE: amino acid
        (D) TOPOLOGY: LINEAR (xi) SEQUENCE DESCRIPTION: SEQ ID NO: 7:

| Ser | Ala | Glu | Pro | Val | Pro | Leu | Gln | Leu | Pro | Pro | Asp | Leu | Arg | Leu | Thr |
|---|---|---|---|---|---|---|---|---|---|---|---|---|---|---|---|
| 1 | | | | 5 | | | | | 10 | | | | | 15 | |

| Leu | Asp | Cys | Asn | Glu | Asp | Cys | Gly | Thr | Ser |
|---|---|---|---|---|---|---|---|---|---|
| | | | 20 | | | | | 25 | |

(2) INFORMATION FOR SEQ ID NO:8:

(i) SEQUENCE CHARACTERISTICS:
        (A) LENGTH: 26 amino acids
        (B) TYPE: amino acid
        (D) TOPOLOGY: LINEAR (xi) SEQUENCE DESCRIPTION: SEQ ID NO: 8:

| Ser | Ala | Glu | Pro | Val | Pro | Leu | Gln | Leu | Pro | Pro | Leu | Glu | Arg | Leu | Thr |
|---|---|---|---|---|---|---|---|---|---|---|---|---|---|---|---|

```
        1               5                  1 0                       1 5
Leu  Asp  Cys  Asn  Glu  Asp  Cys  Gly  Asp  Leu
                    2 0                       2 5
```

(2) INFORMATION FOR SEQ ID NO:9:

(i) SEQUENCE CHARACTERISTICS:
        (A) LENGTH: 26 amino acids
        (B) TYPE: amino acid
        (D) TOPOLOGY: LINEAR (xi) SEQUENCE DESCRIPTION: SEQ ID NO: 9:

```
Ser  Ala  Asp  Leu  Val  Pro  Leu  Gln  Leu  Pro  Pro  Leu  Glu  Arg  Leu  Thr
1                   5                  1 0                       1 5
Leu  Asp  Cys  Asn  Glu  Asp  Cys  Gly  Thr  Ser
                    2 0                       2 5
```

(2) INFORMATION FOR SEQ ID NO:10:

(i) SEQUENCE CHARACTERISTICS:
        (A) LENGTH: 26 amino acids
        (B) TYPE: amino acid
        (D) TOPOLOGY: LINEAR (xi) SEQUENCE DESCRIPTION: SEQ ID NO: 10:

```
Ser  Ala  Glu  Pro  Asp  Leu  Leu  Gln  Leu  Pro  Pro  Leu  Glu  Arg  Leu  Thr
1                   5                  1 0                       1 5
Leu  Asp  Cys  Asn  Glu  Asp  Cys  Gly  Thr  Ser
                    2 0                       2 5
```

(2) INFORMATION FOR SEQ ID NO:11:

(i) SEQUENCE CHARACTERISTICS:
        (A) LENGTH: 26 amino acids
        (B) TYPE: amino acid
        (D) TOPOLOGY: LINEAR (xi) SEQUENCE DESCRIPTION: SEQ ID NO: 11:

```
Ser  Ala  Glu  Pro  Val  Pro  Asp  Leu  Leu  Pro  Pro  Leu  Glu  Arg  Leu  Thr
1                   5                  1 0                       1 5
Leu  Asp  Cys  Asn  Glu  Asp  Cys  Gly  Thr  Ser
                    2 0                       2 5
```

(2) INFORMATION FOR SEQ ID NO:12:

(i) SEQUENCE CHARACTERISTICS:
        (A) LENGTH: 26 amino acids
        (B) TYPE: amino acid
        (D) TOPOLOGY: LINEAR (xi) SEQUENCE DESCRIPTION: SEQ ID NO: 12:

```
Ser  Ala  Glu  Pro  Val  Pro  Leu  Gln  Asp  Leu  Pro  Leu  Glu  Arg  Leu  Thr
1                   5                  1 0                       1 5
Leu  Asp  Cys  Asn  Glu  Asp  Cys  Gly  Thr  Ser
                    2 0                       2 5
```

(2) INFORMATION FOR SEQ ID NO:13:

(i) SEQUENCE CHARACTERISTICS:
        (A) LENGTH: 26 amino acids
        (B) TYPE: amino acid
        (D) TOPOLOGY: LINEAR (xi) SEQUENCE DESCRIPTION: SEQ ID NO: 13:

```
Ser  Ala  Glu  Pro  Val  Pro  Leu  Gln  Leu  Pro  Asp  Leu  Glu  Arg  Leu  Thr
```

```
            1               5                  10                 15
Ser Ala Glu Pro Val Pro Leu Gln Leu Pro Pro Leu Asp Leu Leu Thr
1               5                  10                 15
Leu Asp Cys Asn Glu Asp Cys Gly Thr Ser
                20                  25
```

(2) INFORMATION FOR SEQ ID NO:14:

(i) SEQUENCE CHARACTERISTICS:
        (A) LENGTH: 26 amino acids
        (B) TYPE: amino acid
        (D) TOPOLOGY: LINEAR (xi) SEQUENCE DESCRIPTION: SEQ ID NO: 14:

```
Ser Ala Glu Pro Val Pro Leu Gln Leu Pro Pro Leu Asp Leu Leu Thr
1               5                  10                 15
Leu Asp Cys Asn Glu Asp Cys Gly Thr Ser
                20                  25
```

(2) INFORMATION FOR SEQ ID NO:15:

(i) SEQUENCE CHARACTERISTICS:
        (A) LENGTH: 26 amino acids
        (B) TYPE: amino acid
        (D) TOPOLOGY: LINEAR (xi) SEQUENCE DESCRIPTION: SEQ ID NO: 15:

```
Ser Ala Glu Pro Val Pro Leu Gln Leu Pro Pro Leu Glu Arg Asp Leu
1               5                  10                 15
Leu Asp Cys Asn Glu Asp Cys Gly Thr Ser
                20                  25
```

(2) INFORMATION FOR SEQ ID NO:16:

(i) SEQUENCE CHARACTERISTICS:
        (A) LENGTH: 26 amino acids
        (B) TYPE: amino acid
        (D) TOPOLOGY: LINEAR (xi) SEQUENCE DESCRIPTION: SEQ ID NO: 16:

```
Ser Ala Glu Pro Val Pro Leu Gln Leu Pro Pro Leu Glu Arg Leu Thr
1               5                  10                 15
Asp Leu Cys Asn Glu Asp Cys Gly Thr Ser
                20                  25
```

(2) INFORMATION FOR SEQ ID NO:17:

(i) SEQUENCE CHARACTERISTICS:
        (A) LENGTH: 26 amino acids
        (B) TYPE: amino acid
        (D) TOPOLOGY: LINEAR (xi) SEQUENCE DESCRIPTION: SEQ ID NO: 17:

```
Ser Ala Glu Pro Val Pro Leu Gln Leu Pro Pro Leu Glu Arg Leu Thr
1               5                  10                 15
Leu Glu Asp Leu Glu Asp Cys Gly Thr Ser
                20                  25
```

(2) INFORMATION FOR SEQ ID NO:18:

(i) SEQUENCE CHARACTERISTICS:
        (A) LENGTH: 26 amino acids
        (B) TYPE: amino acid
        (D) TOPOLOGY: LINEAR (xi) SEQUENCE DESCRIPTION: SEQ ID NO: 18:

```
Ser Ala Glu Pro Val Pro Leu Gln Leu Pro Pro Leu Glu Arg Leu Thr
```

```
                 1               5                    1 0                   1 5

Leu  Asp  Cys  Lys  Asp  Leu  Cys  Gly  Thr  Ser
                 2 0                   2 5
```

( 2 ) INFORMATION FOR SEQ ID NO:19:

( i ) SEQUENCE CHARACTERISTICS:
        ( A ) LENGTH: 26 amino acids
        ( B ) TYPE: amino acid
        ( D ) TOPOLOGY: LINEAR ( x i ) SEQUENCE DESCRIPTION: SEQ ID NO: 19:

```
Ser  Ala  Glu  Pro  Val  Pro  Leu  Gln  Leu  Pro  Pro  Leu  Glu  Arg  Leu  Thr
1                5                    1 0                   1 5
Leu  Asp  Cys  Asn  Glu  Glu  Asp  Leu  Thr  Ser
                 2 0                   2 5
```

( 2 ) INFORMATION FOR SEQ ID NO:20:

( i ) SEQUENCE CHARACTERISTICS:
        ( A ) LENGTH: 26 amino acids
        ( B ) TYPE: amino acid
        ( D ) TOPOLOGY: LINEAR ( x i ) SEQUENCE DESCRIPTION: SEQ ID NO: 20:

```
Ser  Ala  Glu  Pro  Val  Pro  Leu  Gln  Leu  Pro  Pro  Ala  Glu  Arg  Leu  Thr
1                5                    1 0                   1 5
Leu  Asp  Cys  Asn  Glu  Asp  Cys  Gly  Thr  Ser
                 2 0                   2 5
```

( 2 ) INFORMATION FOR SEQ ID NO:21:

( i ) SEQUENCE CHARACTERISTICS:
        ( A ) LENGTH: 26 amino acids
        ( B ) TYPE: amino acid
        ( D ) TOPOLOGY: LINEAR ( x i ) SEQUENCE DESCRIPTION: SEQ ID NO: 21:

```
Ser  Ala  Glu  Pro  Val  Pro  Leu  Gln  Leu  Pro  Pro  Leu  Glu  Arg  Ala  Thr
1                5                    1 0                   1 5
Leu  Asp  Cys  Asn  Glu  Asp  Cys  Gly  Thr  Ser
                 2 0                   2 5
```

( 2 ) INFORMATION FOR SEQ ID NO:22:

( i ) SEQUENCE CHARACTERISTICS:
        ( A ) LENGTH: 26 amino acids
        ( B ) TYPE: amino acid
        ( D ) TOPOLOGY: LINEAR ( x i ) SEQUENCE DESCRIPTION: SEQ ID NO: 22:

```
Ser  Ala  Glu  Pro  Val  Pro  Leu  Gln  Leu  Pro  Pro  Leu  Glu  Arg  Leu  Thr
1                5                    1 0                   1 5
Ala  Asp  Cys  Asn  Glu  Asp  Cys  Gly  Thr  Ser
                 2 0                   2 5
```

( 2 ) INFORMATION FOR SEQ ID NO:23:

( i ) SEQUENCE CHARACTERISTICS:
        ( A ) LENGTH: 26 amino acids
        ( B ) TYPE: amino acid
        ( D ) TOPOLOGY: LINEAR ( x i ) SEQUENCE DESCRIPTION: SEQ ID NO: 23:

```
Ser  Ala  Glu  Pro  Val  Pro  Leu  Gln  Leu  Pro  Pro  Ala  Glu  Arg  Ala  Thr
```

```
         1               5                   10                  15
Ala Asp Cys Asn Glu Asp Cys Gly Thr Ser
                     20                  25
```

( 2 ) INFORMATION FOR SEQ ID NO:24:

( i ) SEQUENCE CHARACTERISTICS:
        ( A ) LENGTH: 26 amino acids
        ( B ) TYPE: amino acid
        ( D ) TOPOLOGY: LINEAR ( x i ) SEQUENCE DESCRIPTION: SEQ ID NO: 24:

```
Ser Ala Glu Pro Val Pro Leu Gln Leu Pro Pro Leu Glu Arg Leu Thr
1               5                   10                  15
Leu Asn Ser Asn Glu Asp Cys Gly Thr Ser
                     20                  25
```

( 2 ) INFORMATION FOR SEQ ID NO:25:

( i ) SEQUENCE CHARACTERISTICS:
        ( A ) LENGTH: 26 amino acids
        ( B ) TYPE: amino acid
        ( D ) TOPOLOGY: LINEAR ( x i ) SEQUENCE DESCRIPTION: SEQ ID NO: 25:

```
Ser Ala Glu Pro Val Pro Leu Gln Leu Pro Pro Leu Glu Arg Leu Thr
1               5                   10                  15
Leu Val Cys Asn Glu Asp Cys Gly Thr Ser
                     20                  25
```

( 2 ) INFORMATION FOR SEQ ID NO:26:

( i ) SEQUENCE CHARACTERISTICS:
        ( A ) LENGTH: 26 amino acids
        ( B ) TYPE: amino acid
        ( D ) TOPOLOGY: LINEAR ( x i ) SEQUENCE DESCRIPTION: SEQ ID NO: 26:

```
Ser Ala Glu Pro Val Pro Leu Gln Leu Pro Pro Leu Gln Arg Leu Thr
1               5                   10                  15
Leu Asp Cys Asn Glu Asp Cys Gly Thr Ser
                     20                  25
```

( 2 ) INFORMATION FOR SEQ ID NO:27:

( i ) SEQUENCE CHARACTERISTICS:
        ( A ) LENGTH: 26 amino acis
        ( B ) TYPE: amino acid
        ( D ) TOPOLOGY: LINEAR ( x i ) SEQUENCE DESCRIPTION: SEQ ID NO: 27:

```
Ser Ala Glu Pro Val Pro Leu Gln Leu Pro Pro Leu Val Arg Leu Thr
1               5                   10                  15
Leu Asp Cys Asn Glu Asp Cys Gly Thr Ser
                     20                  25
```

( 2 ) INFORMATION FOR SEQ ID NO:28:

( i ) SEQUENCE CHARACTERISTICS:
        ( A ) LENGTH: 15 amino acids
        ( B ) TYPE: amino acid
        ( D ) TOPOLOGY: LINEAR ( x i ) SEQUENCE DESCRIPTION: SEQ ID NO: 28:

```
Leu Glu Arg Leu Thr Leu Asp Cys Asn Glu Asp Cys Gly Thr Ser
```

1          5                    10                   15

(2) INFORMATION FOR SEQ ID NO:29:

(i) SEQUENCE CHARACTERISTICS:
        (A) LENGTH: 9 amino acids
        (B) TYPE: amino acid
        (D) TOPOLOGY: LINEAR (xi) SEQUENCE DESCRIPTION: SEQ ID NO: 29:

Ser  Ala  Glu  Pro  Val  Pro  Leu  Gln  Asp
1                   5

(2) INFORMATION FOR SEQ ID NO:30:

(i) SEQUENCE CHARACTERISTICS:
        (A) LENGTH: 15 amino acids
        (B) TYPE: amino acid
        (D) TOPOLOGY: LINEAR (xi) SEQUENCE DESCRIPTION: SEQ ID NO: 30:

Leu  Glu  Arg  Leu  Thr  Leu  Asp  Cys  Asn  Glu  Asp  Cys  Gly  Thr  Ser
1                   5                                  10                                 15

(2) INFORMATION FOR SEQ ID NO:31:

(i) SEQUENCE CHARACTERISTICS:
        (A) LENGTH: 9 amino acids
        (B) TYPE: amino acid
        (D) TOPOLOGY: LINEAR (xi) SEQUENCE DESCRIPTION: SEQ ID NO: 31:

Ser  Ala  Glu  Pro  Val  Pro  Leu  Gln  Asp
1                   5

(2) INFORMATION FOR SEQ ID NO:32:

(i) SEQUENCE CHARACTERISTICS:
        (A) LENGTH: 7 amino acids
        (B) TYPE: amino acid
        (D) TOPOLOGY: LINEAR (xi) SEQUENCE DESCRIPTION: SEQ ID NO: 32:

Leu  Glu  Asp  Cys  Gly  Thr  Ser
1                   5

(2) INFORMATION FOR SEQ ID NO:33:

(i) SEQUENCE CHARACTERISTICS:
        (A) LENGTH: 17 amino acids
        (B) TYPE: amino acid
        (D) TOPOLOGY: LINEAR (xi) SEQUENCE DESCRIPTION: SEQ ID NO: 33:

Ser  Ala  Glu  Pro  Val  Pro  Leu  Gln  Leu  Pro  Pro  Leu  Glu  Arg  Leu  Thr
1                   5                                  10                                 15
Asp (2) INFORMATION FOR SEQ ID NO:34:

(i) SEQUENCE CHARACTERISTICS:
        (A) LENGTH: 18 amino acids
        (B) TYPE: amino acid
        (D) TOPOLOGY: LINEAR (xi) SEQUENCE DESCRIPTION: SEQ ID NO: 34:

Ser  Ala  Glu  Pro  Val  Pro  Leu  Gln  Leu  Pro  Pro  Leu  Glu  Arg  Leu  Thr

| 1 | 5 | 10 | 15 |
|---|---|---|---|
| Leu Glu | | | |

CHIMERIC NUCLEIC ACIDS AND PROTEINS FOR INHIBITING HIV-1 EXPRESSION This application is a continuation-in-part of U.S. Ser. No. 08/429,761, filed on Apr. 27, 1995, abandoned, the disclosure of which is incorporated by reference in its entirety.

This invention was made in part with United States government support under grant number AI11772 awarded by the National Institute of Allergy and Infectious Disease. The United States government has certain rights in the invention.

1. FIELD OF THE INVENTION

This invention is in the field of recombinant chimeric nucleic acids and fusion proteins encoded thereby that inhibit human immunodeficiency virus type 1 ("HIV-1") replication in human cells, as well as to host cells expressing the fusion proteins and methods of making and using the same.

2. BACKGROUND OF THE INVENTION

The incidence of acquired immunodeficiency syndrome ("AIDS") caused by human immunodeficiency virus ("HIV-1") continues its worldwide escalation. Despite extensive research, no satisfactory medical method of treatment or prevention has been achieved. HIV-1 is a member of the virus family, Retroviridae, and more specifically of the Lentivirus subfamily. This viral system, along with other related viruses such as HIV-2 and simian immunodeficiencyvirus ("SIV"), have been scrutinized with respect to their molecular biology, immunology, and pathogenesis in an effort to develop safe and efficacious vaccines and antiviral therapies. Nevertheless, attempts to develop an anti-HIV-1 vaccine and anti-HIV-1 chemotherapeutic agents have met with only limited success. Therefore, there is an urgent need to develop new and approaches to combating this lethal viral agent.

Human cells susceptible to HIV-1 infection are tabulated as follows by Levy et al., 1992, *THE MEDICAL MANAGEMENT OF AIDS*, Third Edition, Eds. Sandy et al., W. B. Saunders Company.

TABLE 1

| Hematopoietic | Skin |
|---|---|
| T lymphocytes | Langerhans cells |
| B lymphocytes | Fibroblasts |
| Macrophages | Other |
| Promyelocytes | Renal epithelium |
| Dendritic cells | Colon carcinoma cells |
| Brain | Bowel epithelium |
| Astrocytes | |
| Oligodendrocytes | |
| Capillary endothelium | |
| Macrophages | |

The quantity and quality of HIV-1 gene expression in infected host cells is controlled in large part by the action of two small nuclear viral regulatory proteins termed Tat and Rev (Cullen, 1994, Infectious Agents & Disease 3(2–3) :68–76). Tat is unique among transcriptional transactivatorsin that it acts via a structured RNA target sequence, termed TAR, to induce high levels of transcription from the HIV-1 long terminal repeat promoter element.

The Rev proteins of primate immunodeficiency viruses are essential transactivators to switch from early to late phase in the viral replication cycle (Berchtold et al., 1994, *Virology* 204(1):436–41). The activity of the viral Rev protein is also unprecedented in that this protein functions to induce the nuclear export of incompletely spliced viral transcripts that are otherwise sequestered in the nucleus by the action of cellular factors (Meyer et al., 1994, *Genes & Development* 8(13):1538–47). Like Tat, Rev also interacts with a highly specific cis-acting target sequence termed the Rev Response Element ("RRE") (Cullen, 1994, Infectious Agents & Disease 3(2–3):68–76).

The HIV-1 Rev trans-activator has also been shown to be essential for viral replication in culture (Terwilliger et al., *J. Virol*, 62:655–658, 1988). Rev binds specifically to RRE in incompletely spliced HIV-1 transcripts to permit these nuclear transcripts to be exported to the cytoplasm, where they serve as mRNAs encoding virion structural proteins. When Rev protein is absent from the infected host cell, these essential mRNAs remain confined to the nucleus and the resulting HIV-1 proviruses are unable to produce infectious virions (Feinberg et al., 1986 *Cell:* 46; 807–817; Sadale et al., 1984 *Science*, 239:910–914; Sodroski et al., 1986 *Nature* 321:41 2–417; Terwilliger et al., 1 988,*J. Virol*, 62:655–658.

It has also been shown that dominant negative mutants of the effector domain of Rev act as competitive inhibitors of wild-type Rev function in transfected cells (Malim et al., 1988 *Nature*, 388:254–257). For example, one such dominant negative mutant is the HIV-1 Rev mutant M10, which is localized in the activation domain and is one of the strongest transdominant inhibitors.

It has been proposed that a gene encoding a dominant negative mutant of Rev could be used to treat HIV-1 infection by a process of "intracellular immunization" (Baltimore, 1988, *Nature* 335:395–396) by transforming a patient's own blood line stem cells, ex vivo, to resist HIV-1 infection and reinserting the transformed cells back into the patient. However, the transdominant negative mutant effect is only obtainable when the negative Rev effector domain is present in a large excess. Given the limitations in the quantity of Rev mutant expression vector (or any vector) that can be inserted into a target cell, the requirement for a large excess of a dominant negative mutant to prevent HIV-1 replication limits the potential therapeutic usefulness of this effect (Baltimore, 1988, *Nature* 335:395–396, at page 396, column 1; Malim et al., 1989, Cell 58:205–214).

Thus, there remains a need for an improved method for effectively inhibiting HIV-1 replication in order to treat or prevent HIV-1 infection.

The influenza virus nonstructural viral protein 1 (NS1) has properties that have the potential to provide potent anti-Rev inhibitors.

In contrast to Rev, the influenza virus nonstructural 1 ("NS1") protein inhibits the nuclear export of a spliced viral mRNA, such as the NS2 mRNA (F. V. Alonso-Caplen, M. E. Nemeroff, Y. Qiu, and R. M. Krug, 1992, Genes Dev. 6:255–267). It has also been shown that the NS1 protein binds to the poly(A) sequence at the 3' end of NS2 mRNA and of other mRNAs (Qiu Y. and Krug RM, 1994, Journal of Virology, 68(4):2425–32). In addition, the NS1 protein has been shown to bind to poly(A) itself and to inhibit transport of poly(A)-containing mRNA. In contrast, the NS1 protein failed to inhibit the nuclear export of an mRNA whose 3' end was generated by cleavage without subsequent addition of poly(A). Thus, NS1 requires the presence of poly(A) to inhibit nuclear export of an mRNA.

3. OBJECTS OF THE INVENTION

It is therefore an object of the present invention to provide recombinant chimeric vectors and fusion proteins for the treatment and prevention of HIV-1 infection.

Another object of the present invention is to provide recombinant host cells rendered resistant to HIV-1 infection by the insertion of a chimeric vector able to inhibit HIV-1 virion replication.

It is a further object of the present invention to provide methods for in vivo and ex vivo treatment to prevent HIV-1 infection and to inhibit the progress of HIV-1 infection in an already infected patient.

4. SUMMARY OF THE INVENTION

New compositions and methods for the treatment and prevention of HIV-1 infection are provided. Chimeric nucleic acid molecules encoding fusion proteins having Rev function inhibitory activity and comprising an HIV Rev gene or a Rev fragment or derivative fused to a viral NS1 gene or fragment or derivative is provided. The invention further provides for nucleic acid vectors and fusion proteins for inhibiting the replication of the HIV-1 virus, as well as for host cells expressing the fusion proteins and thereby rendered resistant to HIV-1 infection. The chimeric nucleic acid molecules include, for example, NSM2-Rev, NS-RevM5, NSM2-RevM10, NS-Rev, NSM3-Rev, NSM3-RevM10, NS(M2+M3)-Rev, NS(M2+M3)-RevM10, NSΔ1–6-Rev, NSΔ1–6-RevM10.

Methods for treating or preventing HIV-1 infection include treating a patient with a chimeric nucleic acid molecule encoding a fusion protein having Rev function inhibitory activity and comprising an HIV-1 Rev domain and an influenza A virus NS1 domain, a vector comprising the chimeric nucleic acid molecule. The methods also include treating a patient with the fusion protein encoded by the chimeric nucleic acid molecule or with host cells comprising and expressing the chimeric nucleic acid molecule. The methods of treatment include methods of treatment using chimeric nucleic acid molecules or chimeric proteins comprising NSM2-Rev, NS-RevM5, NSM2-RevM10, NS-Rev, NSM3-Rev, NSM3-RevM10, NS(M2+M3)-Rev, NS(M2+M3)-RevM 10, NSΔ1 -6-Rev, NSΔ1-6-RevM10.

5. DETAILED DESCRIPTION OF THE INVENTION

A fusion protein according to the invention includes NS1 and Rev proteins or fragments or derivatives of the NS1 and Rev proteins. The NS1 protein, fragment or derivative may be directly joined by a peptide bond to the Rev protein, fragment or derivative. Alternatively, the NS1 and Rev components may be linked by a peptide linker ranging in length from one amino acid residue through 75 or more residues. In another alternative, the linker may be an organic polymer.

5.1 BRIEF DESCRIPTION OF THE FIGURES

FIG. 1. Constructs of various NS1 and Rev hybrids. HIV-1 Rev wild type (Rev) or several mutant proteins (RevM5 and RevM 10) were attached to the C-terminal end of NS1 (wild type or mutant NS1). NS1-Rev, fusion protein between wild-type NS1 and wild-type Rev. NSM2-Rev, fusion protein between NSM2 (RNA-binding domain mutant of NS1 ) and wild-type Rev. NSM2-RevM10, fusion protein between NSM2 and RevM10(effector domain mutant of Rev). NSΔ2-RevM5, fusion of NSΔ2 (NS1 with effector domain deletion) with RevM5 (Rev RNA-binding domain mutant). NSD2-Rev, fusion of NSΔ2 with wild-type Rev. B1: RNA binding domain of NS1 protein. B2:Rev RNA binding domain. E1: NS1 effector domain. E2:Rev effector domain. **: amino acid mutation.

Figure 2:
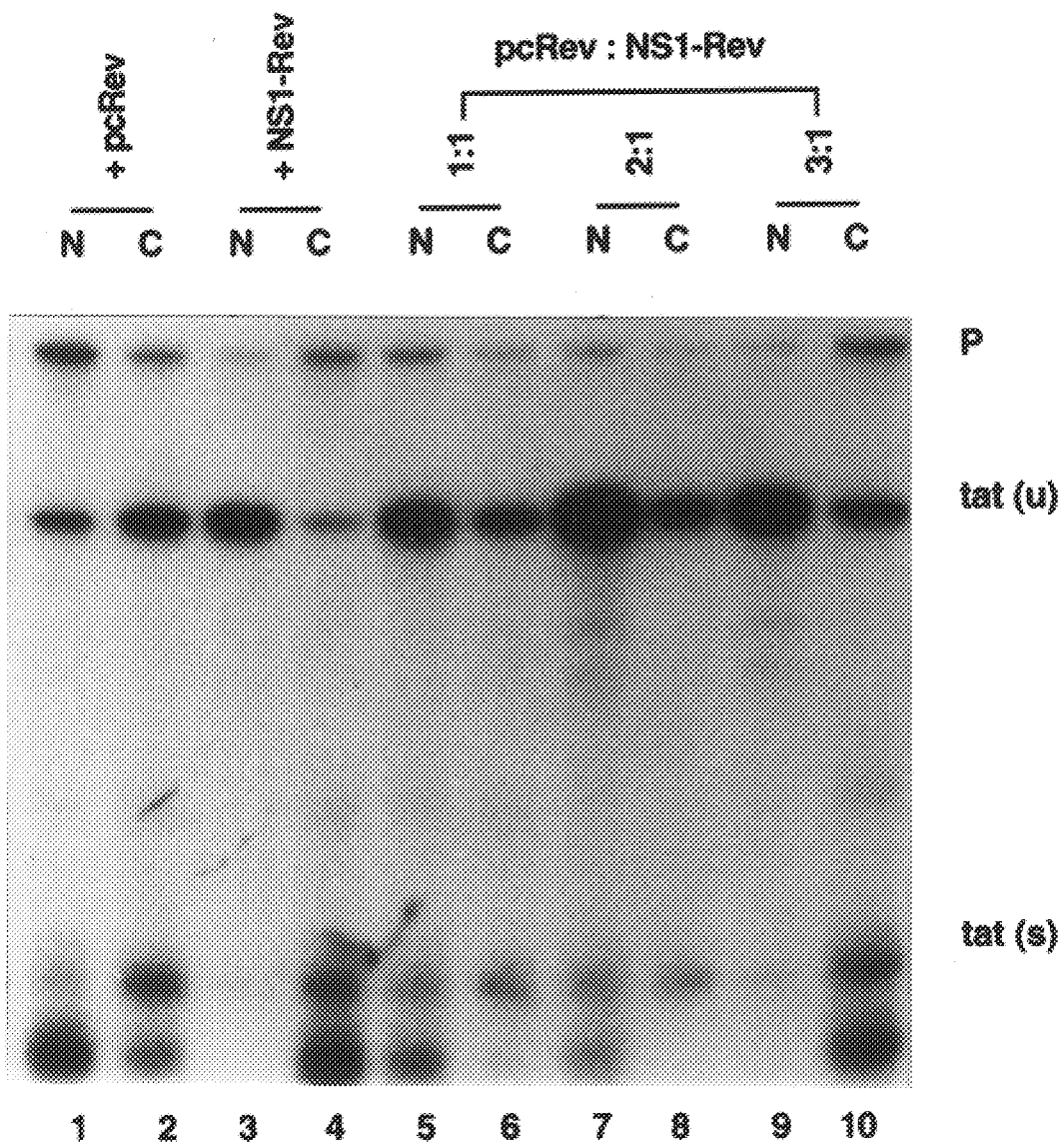

FIG. 2. The effect of wild-type fusion between NS1 and Rev (NS1-Rev) on the transport of tat pre-mRNA. 293 cells were cotransfected with the plasmid encoding the target mRNA (pgtat) and the indicated PBC12 plasmid encoding Rev, NS1-Rev or Rev and NS1-Rev at different ratio (1:1, 2:1 and 3:1). The amount used for each plasmid was 5 μg in each transfection. tat (s), protected fragment for spliced tat mRNA. P, undigested S1 probe.

Figure 3:
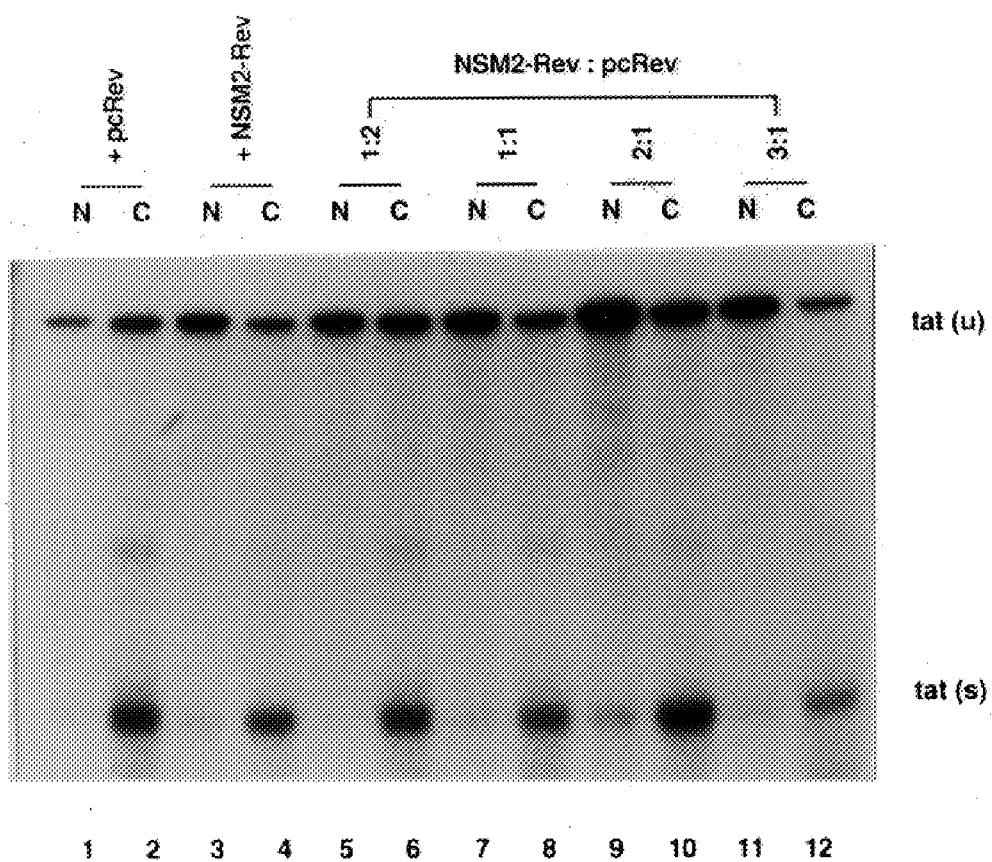

FIG. 3. A hybrid between an NS1 binding domain mutant and wild-type Rev (NSM2-Rev) can reverse the Rev effect on tat pre-mRNA transport. 293 cells were cotransfected with plasmid encoding for the target mRNA (pgtat) and the indicated PBC12 plasmid encoding Rev (lanes 1 & 2), NSM2-Rev (lanes 3 & 4) or NSM2-Rev and Rev at increasing ratio (lanes 5-12). The amount of target plasmid, pgtat, used in each transfection is 5 μg. The amount of plasmid encoding Rev (pcRev) is 5 μ in each transfection. The amount for NSM2-Rev used in each transfection is as following: 5 μg in lanes 3 & 4, 2.5 ,μg in lanes 5 & 6, 5 ,μg in lanes 9 & 10 and 15 μg in lanes 11 & 12. At 40 hours post-transfection, the cells were fractionated into nuclei and cytoplasm, and the nuclear (N) and cytoplasmic (C) RNAs were extracted and subjected to S1 analysis. tat (u), protected fragment for unspliced tat pre-mRNA, tat (s), protected fragment for spliced tat mRNA.

FIG. 4. A hybrid containing mutations in NS1 binding domain and Rev effector domain (NSMA-RevM 10), can reverse Rev effect on tat pre-mRNA transport. The transfection experiment was carried out essentially same as that in FIG. 3, except the NSM2-Rev was replaced by NSM2-RevM 10. P, undigested S1 probe.

FIG. 5. The fusion protein NSΔ2-RevM5 is unable to overcome Rev effect in controlling tat pre-mRNA transport. A mixture of plasmid encoding the target tat mRNA (pgtat) and each indicated plasmid for NS1 (+NS1), Rev (+pcRev) or NSΔ2-RevM5 & pcRev at different ratios were transfected into 293 cells. The amount of pgtat is fixed at 5 μg in each transfection. In lanes 5 through 1 2, constant amount of pcRev (5 μg) is used for each transfection. The amount of NSΔ2-RevM5 used for each transfection is as following: 5 μg in lanes 3 & 4 and 7 & 8, 10 μg in lanes 9 & 10, 20 μg in lanes 11 & 12. The same procedure as shown in FIG. 3 was followed for RNA isolation and S1 analysis. tat (u), protected fragment for unspliced tat pre-mRNA. tat (s), protected fragment for spliced tat mRNA. P, undigested S1 probe.

FIG. 6. The expression of Rev protein in cotransfection with wild-type NS1 and various NS1-Rev hybrids. Plasmid encoding for Rev protein (pcRev) was cotransfected with wild-type NS1 (lanes 3 & 4), NS1-Rev (lanes 5 & 6), NSM2-Rev (lanes 7 & 8), NSM2-RevM10 (lanes 9 & 10) and NSΔ2-RevM5 (lanes 11 & 12) at 1:1 (lanes 3, 5, 7, 9, 11) and 1:2 (lanes 4, 6, 8, 10, 12) ratio, 40 h post-transfection, cell extracts were prepared for Western blot as described below. Rev protein was detected by using polyclonal anti-Rev antibody. Lane 1, blanket control. Lane 2, pcRev alone.

FIG. 7. NSM2 does not inhibit Rev function. The experiment is carried out essentially the same as in FIG. 3 except for the replacement of NSM2-Rev with NSM2.

FIG. 8. The fusion protein NSΔ2-Rev is also unable to overcome Rev effect in controlling tat pre-mRNA transport. 293 cells were cotransfected with plasmid encoding for the target mRNA (pgtat) and the indicated PBC12 plasmid encoding Rev (lanes 1 & 2), NSΔ2-Rev (lanes 3 & 4) or NSΔ2-Rev and Rev at increasing ratio (lanes 5–12). The amount of target plasmid, pgtat, used in each transfection is 5 μg. The amount of plasmid encoding Rev (pcRev) is 5 μg in each transfection. The amount of NSΔ2-Rev used in each transfection is as following: 5 μg in lanes 3 & 4, 2.5 μg in lanes 5 & 6, 5 μg in lanes 7 & 8, 10 μg in lanes 9 & 10 and 15 μg in lanes 11 & 12. The procedure for RNA Isolation and S1 analysis is also described in FIG. 3. tat (u), protected fragment for unspliced tat pre-mRNA. tat (s), protected fragment for spliced tat mRNA. P, undigested S1 probe.

FIG. 9A–9B. The upper panel (A) shows Rev mutants M9-M36(SEQ ID NOS:5–34). The lower panel (B) shows NSI mutants 1–18(SEQ ID NO:4).

Figure 10:
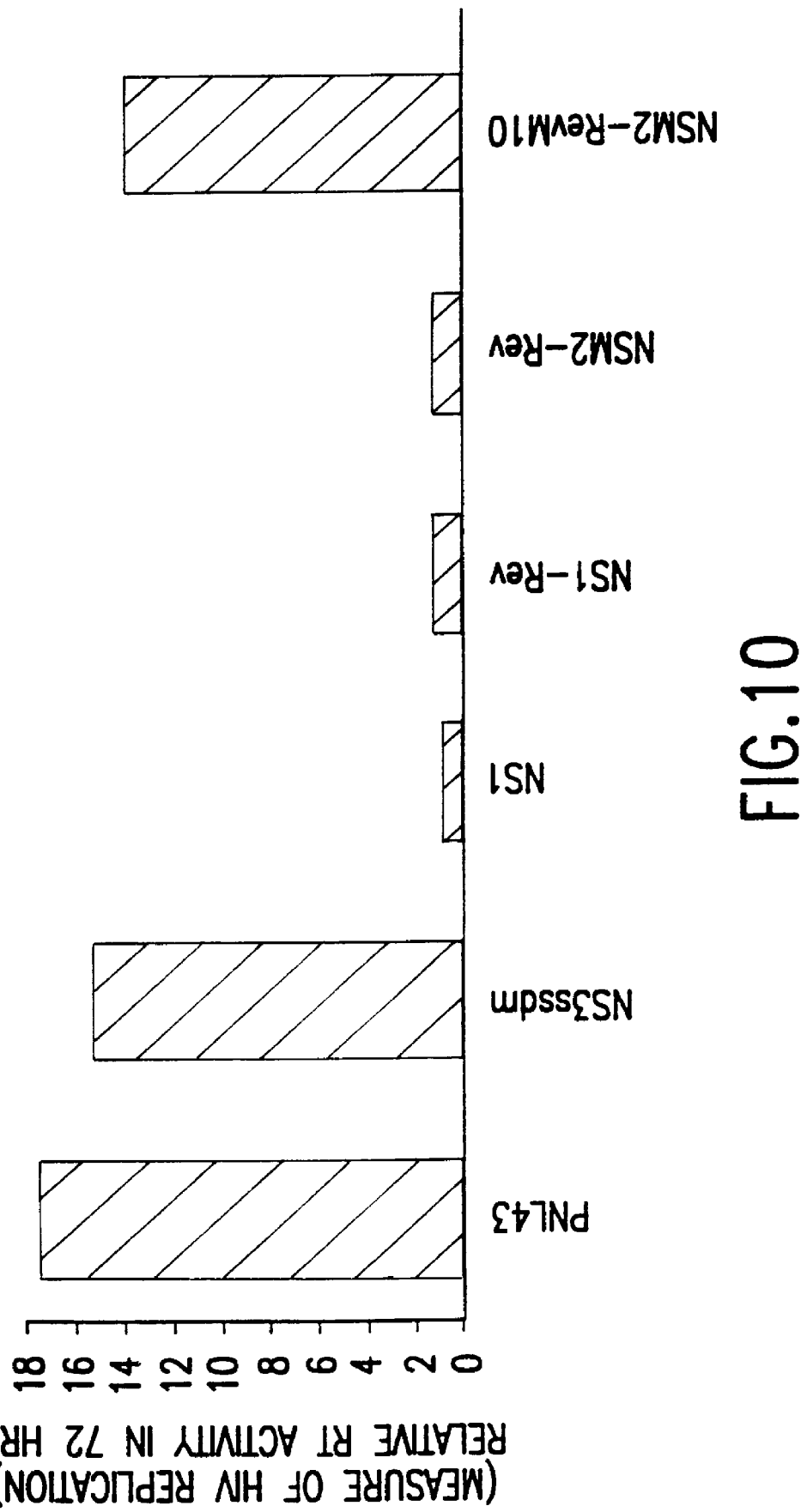

FIG. 10. Shows co-transfection of 393 cells with full-length HIV-1 alone (PNL43) and HIV-1 co-transfected with NS1, NS1-Rev, NSM2-Rev and NSM2-RevM10over a 72 hour period. HIV-1 replication was determined by measurement of reverse transcriptive enzyme produced by HIV-1 infected cells.

5.2 HIV-1 Rev and NS1 Proteins

The influenza virus NS1 protein is the only known example of a protein that inhibits the nuclear export of mRNA. The NS1 protein has two functional domains: an RNA-binding domain and a second domain which is most likely the effector domain (also referred to herein as the activation domain) (Qian et al., 1994, *Journal of Virology* 68(4):2433–2441). The RNA-binding domain of the NS1 protein does not have any evident homology with other known RNA-binding domains. It has been suggested (Qian et al., *Journal of Virology* 68(4):2433–2441)that the second functional domain is the effector domain, the domain that interacts with cellular nuclear targets to carry out the function of inhibiting the nuclear export of mRNA. The HIV-1 Rev protein, which also regulates the nuclear export of RNA, has a functional domain separate from its RNA-binding domain, and this second domain, termed the effector domain, is presumed to interact with those nuclear proteins to accomplish the regulation of the nuclear export of viral pre-mRNAs. These putative cellular proteins have not yet been identified, and consequently the mechanism of action of the Rev effector domain has not yet been established.

Unlike the effector domain mutants of the HIV-1 Rev protein, the effector domain mutants of the NS1 protein, both point mutations and deletions, are not dominant negative versus the wild-type NS1 protein (Hope et al., 1992,*Journal of Virology,* 66:1849–1855). With at least one Rev protein, the Visna virus Rev protein, effector domain mutants exhibited only a weakly dominant negative phenotype (Tiley et al., 1991,*Journal of Virology* 65:3877–3881). Consequently, a dominant negative phenotype may not be a common property of effector domain mutants of proteins that regulate nuclear mRNA export.

The two types of proteins that regulate the nuclear export of mRNA, lentivirus Rev (and Rev-like) proteins and the influenza virus NS1 protein, have the common property of containing two functional domains, an RNA-binding domain and an effector domain. However, there are several significant differences between the effector domains of the NS1 and Rev proteins. These differences most likely indicate that the cellular nuclear target(s) and the function of the effector domains of the NS1 and Rev proteins are quite different. It has been previously suggested that one consequence of such a difference is that the NS1 and Rev proteins have opposite effects on nuclear mRNA transport. However, it was not previously known, and there has previously been no basis to predict that NS1 can counteract the nuclear mRNA transport properties of HIV-1 Rev (Qian et al., 5 1994, *Journal of Virology* 68(4):2433–2441).

5.3 Fusion Proteins

The HIV-1 Rev protein and the influenza A virus NS1 protein are well known to the art. The nucleic acid sequences encoding these proteins are known and chimera nucleic acid sequences encoding fusion proteins may be readily constructed by art known techniques (Chaudhary et al, 1989, *Nature* 339:394–397). For HIV-1 Rev, the sequence is disclosed, e.g., by Malim et al., 1989, Cell 58:205–214. For influenza NS1, the sequence is disclosed, e.g., by Qian et al., 1994, *Journal of Virology.* 68(4):2433–2441. Further, the chimeric nucleic acid molecules may be prepared with sections encoding a linking peptide connecting the NS1 and Rev protein portions of the encoded fusion protein. Optionally, the peptide linker may be selected to include residues imparting stearic flexibility in order to enhance the function of the fusion protein.

The present invention is directed to genes and their encoded proteins which regulate the replication of HIV-1 virus in a host cell. The proteins of the present invention i.e., the NS1-Rev proteins, include fusion proteins formed from all possible combinations of influenza A virus NS1, mutant influenza A NS1, HIV-1 Rev protein, mutant HIV-1 Rev proteins and fragments thereof. Known mutant Rev proteins are shown in FIG. 9. NS1 mutants include the M2 and M3 mutants, described below at Section 6.1. The NS1 and Rev protein portions of the fusion protein can be assembled so that the NS1 is linked to the carboxy terminus of the Rev protein or so that the Rev protein is linked to the carboxy terminus of the NS1 protein, provided that the resulting fusion protein has Rev protein inhibitory activity. The fusion proteins may comprise the complete mature influenza A virus NS1 and HIV-1 Rev proteins, or may comprise fragments or domains of the influenza A virus NS1 and HIV-1 Rev proteins, respectively.

The effector and binding domains of the influenza A virus NS1 protein are shown by Qian et al., 1994, *Journal of Virology,* 68(4) 2433–2441, the disclosure of which is incorporated by reference herein in its entirety. The effector and binding domains of the HIV-1 Rev protein are shown by Malim et al., 1989, *Cell* 58:205–214, the disclosure of which is incorporated by reference herein in its entirety.

Thus, the fusion proteins include, but are not limited to, the following combinations wherein Rev is attached to the C-terminal of NS1. NS1-Rev is a fusion protein between wild-type NS1 and wild-type Rev. NSM2-Rev is a fusion protein between NSM2 (an RNA-binding domain mutant of NS1) and wild-type Rev. NSM2-RevM10 is a fusion protein between NSM2 and RevM10 (an effector domain mutant of Rev). NSΔ2-RevM5 is a fusion of NSΔ2 (NS1 with effector domain deletion) with RevM5 (Rev RNA-binding domain mutant). NSD2-Rev is a fusion of NSΔ2 with wild-type Rev.

In a preferred embodiment the fusion protein is formed from the NS1-1 binding domain mutant and the HIV-1 Rev is the complete wild-type protein.

5.4 Fusion Protein Linkers

The components of the fusion protein may be operatively linked directly one to the other wherein the NS1 portion is linked to the carboxy terminal of the Rev protein or the Rev portion may be linked to the carboxy terminal of the Rev portion of the fusion protein. The two protein components of the fusion protein may be directly linked via an amino terminus to carboxy terminus peptide bond.

Alternatively, one or more linker molecules connect the two portions of the fusion protein. The linker molecule allows the two portions of the fusion protein increased stearic freedom to enhance the ability of the NS1 and Rev domains to bind to active sites. In one embodiment the linkers are peptide linkers. Peptides for linking protein chains are well known to the art (Huston et al., 1993, *Immunotechnology*, ed. by J. Gosling et al., 47–60; Huston et al., *Molecular Design and Modeling: Concepts and Applications*, Part B, ed. J. J. Langone, *Methods in Enzymology* 203:46–88; Chaudhary et al, 1989, *Nature* 339:394–397). For example, a DNA construct is prepared by well known recombinant methods or by the polymerase chain reaction.

The DNA construct sequentially, 5' to 3', encodes a first part of a proposed fusion protein, then a peptide linker region, followed by a second part of a proposed fusion protein as a single open reading frame, flanked by regulatory elements suitable for expressing the encoded fusion protein in a host cell.

In one embodiment a peptide of from 1 to 10 amino acid residues serves as a linker. In a further embodiment, a peptide of from 10 to 50residues serves as a linker. In a preferred embodiment, a peptide of from 5 to 100 or more residues serves as a linker. The peptide linker according to the invention may optionally include proline, glycine or other residues that will act as "molecular hinges" to allow greater stearic freedom for the NS1 and Rev parts of the fusion protein in order to enhance the function of the fusion protein.

The peptide linker may be encoded by the chimeric nucleic acid molecule, or the NS1 and Rev protein parts may be prepared separately and the fusion protein assembled by peptide chemical methods well known to the art.

In another alternative, the linker molecule may be comprised of peptide and nonpeptide polymers or may be exclusively non-peptide in composition. A wide variety of organic linkers are well known to the art and available to link NS1 and Rev proteins as required. For example, polyalkane polymers (e.g., —$(CH_2)_n$—) may be readily linked by well known methods to thiol groups on sulfhydral containing amino acids.

5.5 Vectors and Promotors

The present invention further relates to vectors expressing the fusion proteins according to the invention. The vectors may be selected from any suitable vectors for inserting nucleic acid molecules into human host cells. The vectors may be deoxyribonucleic acid ) ("DNA") vectors such as plasmids, adenovirus or even naked DNA inserted directly into cells to be treated by art known methods. The vectors may also be ribonucleic acid ("RNA") vectors, such as safe strains of the retroviruses.

Any of the methods known to the art for the insertion of nucleic acid molecular fragments into a vector, as described, for example, in Maniatis, T., Fritsch, E. F., and Sambrook, J. (1989): *Molecular Cloning (A Laboratory Manual)*, Cold Spring Harbor Laboratory, Cold Spring Harbor, N.Y.; and Ausubel, F. M., Brent, R., Kingston, R. E., Moore, D. D., Seidman, J. G., Smith, J. A., and Struhl, K. (1992): *Current Protocols in Molecular Biology*, John Wiley & Sons, New York, may be used to construct NS1-Rev fusion protein-encoding expression vectors consisting of appropriate transcriptional/translational control signals. These methods may include in vitro DNA recombinant and synthetic techniques and in vivo genetic recombination. Expression of a nucleic acid sequence encoding NS1 -Rev fusion proteins may be regulated by a second nucleic acid sequence so that the NS1-Rev fusion protein is expressed in a host infected or transfected with the recombinant chimeric nucleic acid molecule. For example, expression of NS1-Rev fusion proteins may be controlled by any promoter/enhancer element known in the art. The promoter activation may be tissue specific or inducible by a metabolic product or administered substance.

Promoters/enhancers which may be used to control NS1-Rev fusion protein gene expression include, but are not limited to, the native HIV-1 promoter, the cytomegalovirus (CMV) promoter/enhancer (Karasuyama, H., et al., 1989, *J. Exp. Med.*, 169:13), the human β-actin promoter (Gunning, et al., 1987, *Proc. Nati. Acad. Sci. USA*, 84:4831–4835), the glucocorticoid-inducible promoter present in the mouse mammary tumor virus long terminal repeat (MMTV LTR) (Klessig, D. F., et al., 1984, *Mol. Cell Biol.*, 4:1354–1362), the long terminal repeat sequences of Moloney murine leukemia virus (MuLV LTR) (Weiss, R., et al., 1985, RNA Tumor Viruses, Cold Spring Harbor Laboratory, Cold Spring Harbor, N.Y.), the SV40 early region promoter (Bernoist and Chambon, 1981, *Nature* 290:304–310), the promoter contained in the 3' long terminal repeat of Rous sarcoma virus (RSV) (Yamamoto et al., 1980, *Cell* 22:787–797), the herpes simplex virus (HSV) thymidine kinase promoter/enhancer (Wagner et al., 1981, *Proc. Natl. Acad. Sci. U.S.A.* 78:1441–1445), the regulatory sequences of the metallothionein gene (Brinster et al., 1982, *Nature* 296:39–42), the adenovirus promoter (Yamada et al., 1985, *Proc. Natl. Acad. Sci. U.S.A.* 82(11):3567–71), and the herpes simplex virus LAT promoter (Wolfe, J. H., et al., 1992, *Nature Genetics,* 1:379–384).

Expression vectors compatible with mammalian host cells for use in genetic therapy of cells to inhibit or treat HIV-replication, include, but are not limited to: plasmids, retroviral vectors, adenovirus vectors, herpes viral vectors, poxvirus vectors and non-replicative avipox viruses, as disclosed, for example, by U.S. Pat. No. 5,174,993. The viral vectors may be suitably modified for safety, as is well known to the art, in order that they be non-replicative in human host cells.

5.6 Assays for HIV Rev Activity

In order to determine the optimum NS1 -Rev fusion protein for inhibiting HIV-1 replication in host cells, HIV-1 Rev activity is determined with and without co-transfection into host cells with a chimeric nucleic acid encoding a fusion protein to be tested. Such assays are described in the art (Malim et al., 1988, Nature 335:401–456; Malim et al., 1989, Nature 338:254–257).

For example, the relative level of expression of the tested Rev proteins in transfected cells is determined by immunoprecipitation of $^{35}S$-cysteive labeled cultures in the presence and absence of co-transfection in COS cell cultures (Malim et al., 1989, *Cell* 58:205–214).

5.7 Methods of Treatment

The present invention is also directed to methods of treatment for preventing or inhibiting the progression of HIV-1 virus infection in primates and in particular, in humans. Methods of treatment include the direct introduction of the chimeric nucleic acid or the expressed protein into the cells of the person to be treated.

Alternatively, the methods of treatment include the ex vivo treatment of cells, e.g., bone marrow, including hematopoietic stem cells or peripheral blood cells that have been removed from a patient's body, followed by the reintroduction of the treated cells into the patient. The ex vivo treatment can be conducted with the fusion protein according to the invention, in order to inhibit the replication of HIV-1 virus in the treated tissue, e.g., blood or bone marrow. In addition, the ex vivo treatment can be conducted with the chimeric nucleic acid molecules according to the invention, in order that the reintroduced cells, e.g., from blood or bone marrow, will continue to resist HIV-1 infection after reintroduction.

In another embodiment, vectors according to the invention can be applied to the skin and internal organs by suspension in appropriate physiological carriers.

For example, a physiologically appropriate solution containing an effective concentration of active vectors can be administered topically, intraocularly, parenterally, orally, intranasally, intravenously, intramuscularly, subcutaneously or by any other effective means. In particular, the vector may be directly injected into a target tissue by a needle in amounts effective to treat the cells of the target tissue. Alternatively, a body cavity such as in the eye, gastrointestinal tract, genitourinary tract (e.g., the urinary bladder), pulmonary and bronchial system and the like can receive a physiologically appropriate composition (e.g., a solution such as a saline or phosphate buffer, a suspension, or an emulsion, which is sterile except for the vector) containing an effective concentration of active vectors via direct injection with a needle or via a catheter or other delivery tube placed into the cancer or tumor afflicted hollow organ. Any effective imaging device such as X-ray, sonogram, or fiberoptic visualization system may be used to locate the target tissue and guide the needle or catheter tube.

In another alternative, a physiologically appropriate solution containing an effective concentration of active vectors can be administered systemically into the blood circulation to treat cells or tissues which cannot be directly reached or anatomically isolated.

In yet another alternative, target cells can be treated by introducing a fusion protein according to the invention into the cells by any known method. For example, liposomes are artificial membrane vesicles that are available to deliver drugs, proteins and plasmid vectors both in vitro or in vivo (Mannino, R. J. et al., 1988, *Biotechniques,* 6:682–690) into target cells (Newton, A. C. and Huestis, W. H., *Biochemistry,* 1988, 27:4655–4659;Tanswell, A. K. et al., 1990, *Biochemica et Biophysica Acta,* 1044:269–274; and Ceccoll, J. et al. *Journal of Investigative Dermatology,* 1989, 93:190–194). Thus, fusion protein can be encapsulated at high efficiency with liposome vesicles and delivered into mammalian cells in vitro or in vivo.

Liposome-encapsulated fusion protein may be administered topically, intraocularly, parenterally, intranasally, intratracheally, intrabronchially, intramuscularly, subcutaneously or by any other effective means at a dose efficacious to treat the abnormally proliferating cells of the target tissue. The liposomes may be administered in any physiologically appropriate composition containing an effective concentration of encapsulated fusion protein.

An effective concentration of vector or fusion protein may be readily determined by the ordinary artisan, for example, by screening chimeric nucleic acid vectors encoding fusion protein, or a fusion protein, in an HIV-1 assay system as described hereinbelow. Essentially, COS cells are infected with HIV-1 and the reverse transcriptase levels are followed for 72 hours. The HIV-1 infected cells are compared to HIV-1 infected cells treated with vector or fusion protein and a dose-response curve is determined.

The invention is further described in the following examples which are in no way intended to limit the scope of the invention.

6. EXAMPLES

6.1 Construction of Nucleic Acid Chimeras Comprising NS1 and Rev Genes

Expression plasmids for NS1-Rev fusion proteins and their derivatives were HIV-1 Rev (pcRev) and several Rev mutants (pcRevM5 and pcRevM10) were generously provided by Drs. Bryan R. Cullen and Michael H. Malim. The wild-type and mutant Rev genes were amplified by PCR while adding Sfu 1 sites at both termini. The Sfu 1 PCR fragment of Rev and the Rev mutants (RevM5 and RevM10) were cloned in-frame into PBC12NS3ss or the plasmids encoding the NS1 mutant proteins at the unique Sfu 1 site near the carboxyl terminal.

Influenza NS1

The NS1 DNA sequence of about 860 nucleotides and the predicted amino acid sequence are as described by Lamb et al, 1980, *Cell* 21:475–485, the disclosure of which is incorporated by reference herein in its entirety. NS3ss is an NS1 mutation that is modified at the 3' splice site, relative to NS1, to prevent splicing. NS3ss as used herein has an A to C mutation at nucleotide sequence 527 relative to the Lamb et al. NS1 sequence and an A to G mutation at nucleotide 530, relative to the Lamb et al. sequence, to provide an Smal restriction site.

The NS1 M2 mutant as used herein has the following mutation relative to the NS3ss sequence beginning at nucleotide 80, so that CCG AAA is changed to AGC TGC. The NS1 M3 mutant has a C to G mutation at nucleotide 117, relative to the NS3ss sequence and the sequence at nucleotides 20, 21 and 22 are changed to GCT, relative to the NS3ss sequence.

HIV-1 Rev

DNA coding sequence for the wild-type Rev is derived from a 31008 dalton Sal I to Xho I fragment of a proviral HXB-3 HIB-1 clone as disclosed by Malim et al., 1988, *Nature* 335:181–183. The Rev sequence is disclosed by Shaw et al., 1987, *Science,* 226:1165–1171 and Ratner et al., 1987, *AID Res.* 3:57–69, the disclosures of which are incorporated by reference herein in their entirety. The HIV-1 Rev activation domain sequence is provided by Malim et al., 1991, *Journal of Virology* 65:4248–4254, the disclosure of which is incorporated by reference herein in its entirety, who also provide, at FIG. 1, the definition of each of HIV-1 mutants M9 through M36 along with a tabulation of the in vivo phenotype for each. The Rev mutants, including M5 are also described by Malim et al., 1989, *Cell* 58:205–214, at FIG. 1.

Construction of the Chimeric Nucleic Acid Molecules

All of the chimeric nucleic acid molecules encoding HS1-Rev fusion proteins were prepared as follows.

The nucleotides encoding amino acid residues 231–237 were cut from the C-terminus of the NS1 gene by Asull or Sfu (GTT/GCA). The 5' terminus of the Rev gene was mutated by PCR to insert an SfuI or AsuII restriction site. Thus, TTAGGCATCTCCTATG --PCR-- >TGTT*CGAACTCCTATG(* is restriction site)(SEQ ID NOS:1 and 2). The NS1 gene was then ligated to the 5' terminus of the Rev gene by standard methods to provide the following fusion protein.

GTT/CGA/ACT/CCT/ATG -(SEQ ID NO:3)
NS1/NS1/
230/231
Val/Arg so that the codon for the 231 Arg residue is regenerated. The ACT and CCT encode threonine and proline, respectively, and form a dipeptide linker between the NS1 and Rev parts of the fusion protein.

6.2 Cell culture and Transfection 293 cells were maintained in Dulbecco's Modified Eagle Medium (DMEM) containing 10% fetal calf serum and were transfected using the calcium phosphate method (Davis et al., 1986, *Methods in Molecular Biology*, Elseview Science Publishing, New York). The level of plasmid DNA used in each transfection experiment is indicated in the appropriate figure legend.

6.3 RNA Extraction and S1 Assay

Transfected 293 cells were harvested 40 hours post-transfection. The cells were fractionated into nuclei cytoplasm by using a dunce homonaginizer, as described previously (Alonso-Caplen et al., 1992, Genes Dev. 6:255–267). The fractionation was monitored by agarose gel analysis to determine the presence of rRNA markers characteristic of the nucleus (45S) and of the cytoplasm (18S). RNA was extracted using the guanidinium isothiocyanate method (Chomcynskiet al., 1987, *Anal. Biochem* 162:156–159). The amount of RNA in the cytoplasm and nucleus was determined both by absorbance at 260 nm and by quantitating the ethidium stained agarose gel analysis of the cytoplasmic and nuclear RNAs. Cell-equivalent amounts of nuclear and cytoplasmic RNAs were assayed by S1 nuclease protection using 5' end-labeled single-stranded DNA probes (Davis et al., 1986). The SalI - BamHl fragment from pgtat was cloned into M13mp9 at SalI- BamHl sites. A primer oligonucleotide which was complementary to the tat sequence at the 3' end was kinased at the 5' end with [$\gamma$-$^{32}$P] ATP and was annealed to the single-stranded M13 DNA template. After primer extension using the Klenow fragment followed by Nar 1 digestion, the probe was purified on an alkaline-denaturing agarose gel. This probe only detects the tat mRNA and not the Rev mRNA. After S1 nuclease digestion, the protected fragment(s) were resolved by denaturing polyacrylamide gel electrophoresis (7% polyacrylamide-7 urea).

6.4 Western Blot 292 cells in 60-mm culture dish transfected with pcRev and the NS1-Rev fusion plasmids were harvested after 40 h incubation. The cells were washed with PBS and suspended in 500 $\mu$l of IPP$_{150}$ (Hamm et al., 1987, Monomethyllated Cap Structures Facilitate RNA Export From the Nucleus, *Cell*, 63:109–118) containing 150 mM NaCl and 0.1 % NP-40 and sonicated briefly. 25 $\mu$l of each sample were loaded on a SDS-polyacrylamide gel. The Western blotting protocol from Amersham Polyclonal anti-Rev antibody was a gift from Dr. Michael H. Malim.

6.5 NS1 is Dominant Over Rev In Controlled mRNA Transport

HIV-1 protein expression is required for viral replication by inducing selectively the functional expression of the incompletely spliced HIV-1 mRNAs that encode the viral structural proteins (Gag and Env). NS1 inhibits mRNA export from the nucleus, and Rev facilitates RRE containing HIV viral pre-mRNA export from the nucleus. It, accordingly, it was determined whether the NS1 protein was able to inhibit the Rev effect on pre-mRNA transport, using transfection experiments. Plasmids containing pcRev or NS1 (providing the protein source) and a genomic clone encoding tat pre-mRNA (pgtat) were cotransfected into 293 cells. The nuclear/cytoplasmic distribution of unspliced target tat mRNA [tat (u)] was determined. pcRev facilitated the export of unspliced tat mRNA from the nucleus. In the NS1 transfected cells, the unspliced tat mRNA were retained in the nucleus. When plasmid encoding wild-type Rev (pcRev) was mixed with NS1 at an increasing ratio and cotransfected with pgtat (even at 3:1 of pcRev to NS1), pcRev still reverses the inhibitory effect of NS1 on the unspliced tat mRNA retained in the nucleus. This indicated in the competition between NS1 and Rev, NS1 was dominant. This was confirmed by western blot which showed that the expression level of Rev protein in cotransfection with NS1 in FIG. 6, lanes 3 and 4, when cotransfect the pcRev and SN1 plasmid at 1:1 (lane 3) and 1:2 ratio (lane 4), the Rev protein expression was about 3–4 fold lower than the control (lane 2, transfected with pcRev alone). Hence, the wild-type NS1 protein acted at least partially at the level of synthesis of the Rev protein.

6.6 Wild-Type NS1 and Wild-Type Rev

A hybrid between wild-type NS1 and wild-type Rev, NS1-Rev (FIG. 1), was used as a protein source (FIG. 2). In lanes 1 and 2, pcRev facilitated the tat pre-mRNA [tat(u)] export from the nucleus. When the NS1-Rev was synthesized, unspliced tat mRNA remained in the nucleus (lanes 3 & 4). Even at high pcRev to NS1-Rev ratio (from 1:1 to 3:1), no Rev effect was observed (lanes 5–10) and the unspliced tat mRNA [tat(u)] was retained in the nucleus. This indicates that even when wild-type NS1 and Rev were fused together with both of their functional domains intact, NS1 was still dominant over Rev in controlling the nuclear export of mRNA. When cotransfected with NS1-Rev, Rev protein expression was inhibited slightly, resulting an one to two-fold reduction compared to control (FIG. 6), complete lanes 5 & 6 with lane 2) so that at least some of the dominance of NS1-Rev may be due to its inhibition of Rev synthesis.

6.7 Mutant NS1 and Wild-Type Rev or Rev Effector Domain Mutant

Figure 4:
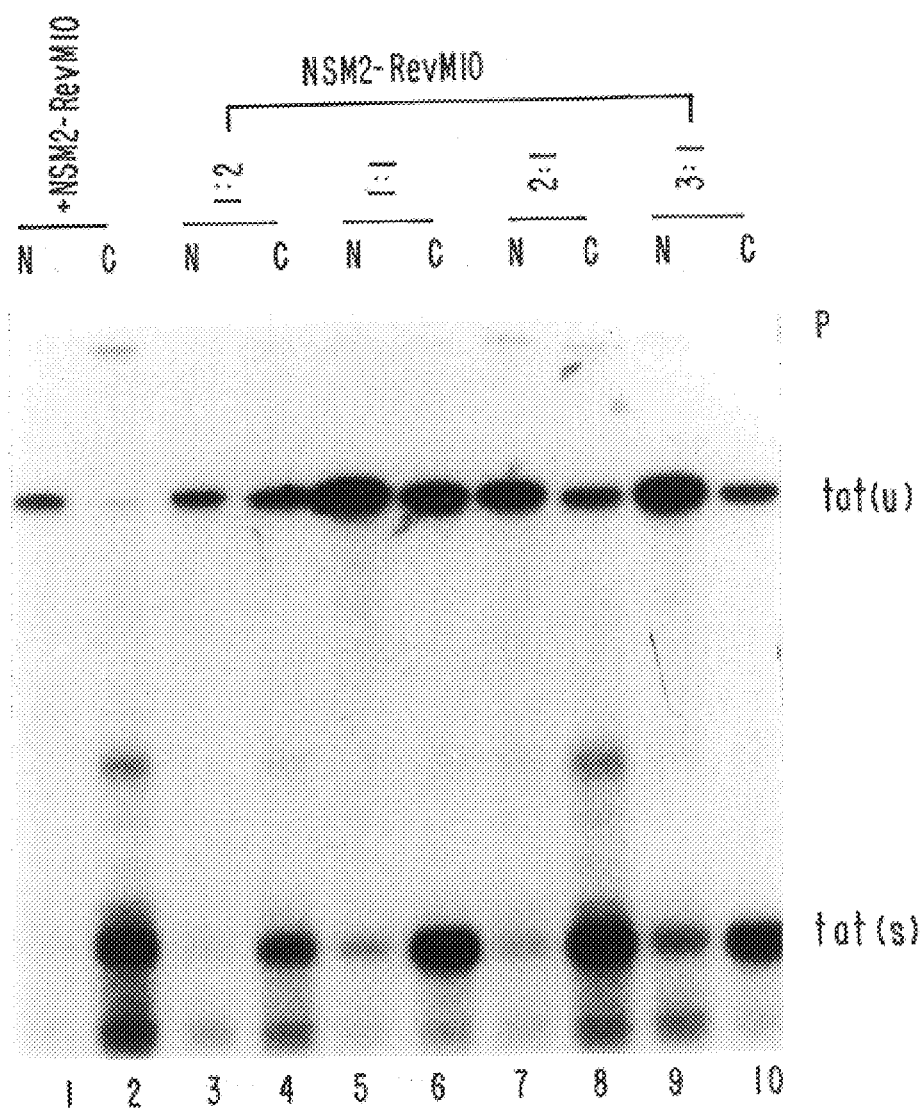

Since NS1 has inhibitory effects on both mRNA transport and pre-mRNA splicing, which do not distinguish between viral or cellular mRNAs, wild-type NS1 is not the best choice for Rev inhibition. To circumvent this problem, two hybrid proteins were prepared using the RNA binding domain mutant of NS1 protein which no longer inhibits nuclear export and pre-mRNA splicing. The first hybrid, NSM2-Rev (FIG. 1), is a hybrid between NS1 mutant 2 and wild-type Rev protein. The second hybrid, NSM2-RevM10 (FIG. 1), is a hybrid between NS1 mutant 2 (RNA binding domain mutant) and Rev mutant 10 (Rev effector domain mutant) (Malim et al., 1989, *Cell*, 58, 205–214). When cotransfected with NSM2-Rev, unspliced tat mRNA [tat(u)] was retained in the nucleus (FIG. 3, lanes 3 & 4). Although NSM2-Rev was not as potent as NS1 or NS1-Rev in terms of inhibiting Rev function (compare with FIG. 2), NSM2-Rev reverses the Rev effect at 1:1 NSM2-Rev to Rev ratio (lanes 7 & 8), and at a 3:1 ratio the inhibitory effect was very clear (lanes 11 & 12). As shown in FIG. 4, NSM2-RevM10 also reverses Rev effector on unspliced tat mRNA transport, at a 3:1 ratio of NSM2-RevM10to Rev ratio,the majority of the unspliced tat mRNA retained in the nuclei.

Figure 5:
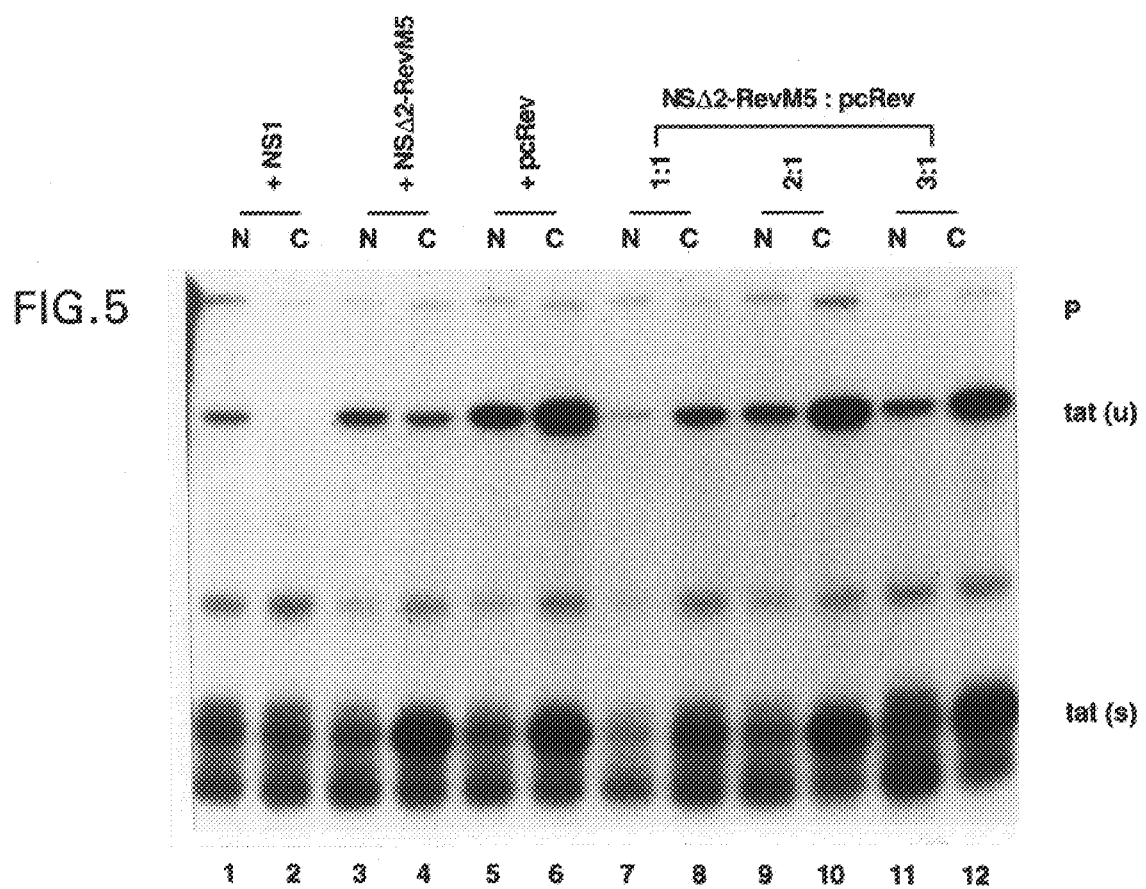

As a control, a fusion between an NS1 effector domain deletion mutant (NSΔ2) and a Rev RNA binding domain mutant (RevM5) was used as protein source (NSΔ2-RevM5) (FIG. 1). The same set of transfections were performed (FIG. 5). NSΔ2-RevM5 was not able to reverse Rev function. Even at a 3:1 ratio of NSΔ2-RevM5 to Rev, unspliced tat mRNA was still effectively transported from the nuclei (lanes 11 & 12). This indicates that the effector domain of the NS2 protein was required for the inhibition of Rev function.

Figure 6:
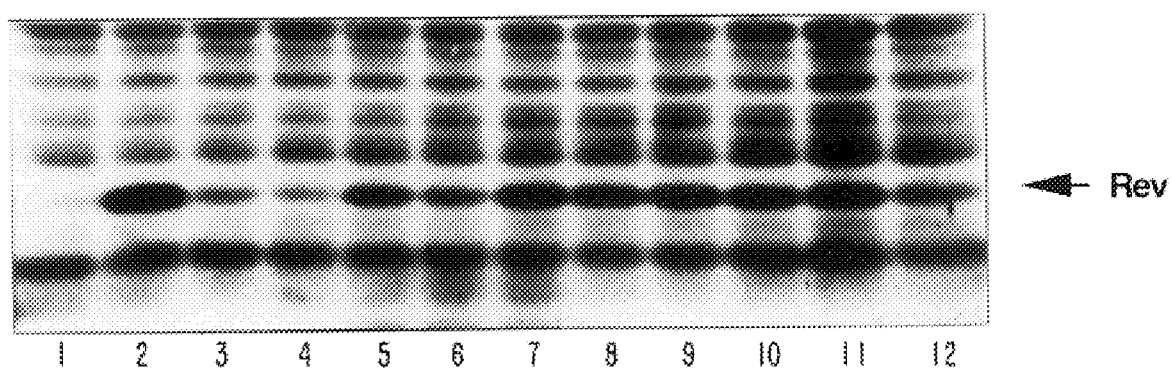

The synthesis of the Rev protein was determined by Western blot (FIG. 6). The quantities of Rev protein expression were comparable between each cotransfection and control (Rev alone) (lane 2). This indicates that the inhibitory effects of NSM2-Rev (lanes 7 & 8) and NSM2-RevM 10 (lanes 9 & 10) were not due to the inhibition of Rev synthesis. The two fusion proteins were therefore most likely inhibiting the function of the Rev protein. The apparent lower Rev expression in lanes 3 & 4 probably reflects the inhibition of pcRev nuclear export by wild-type NS1 protein.

Figure 7:
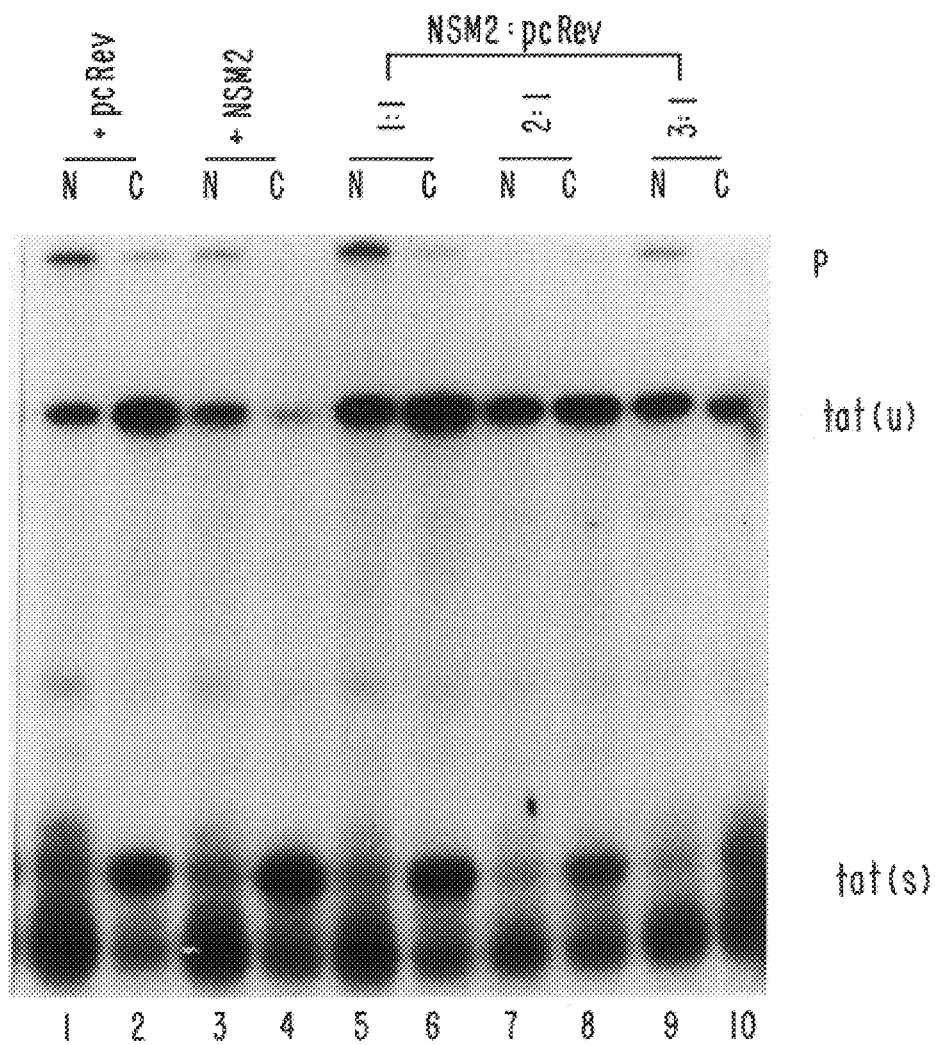
Figure 8:
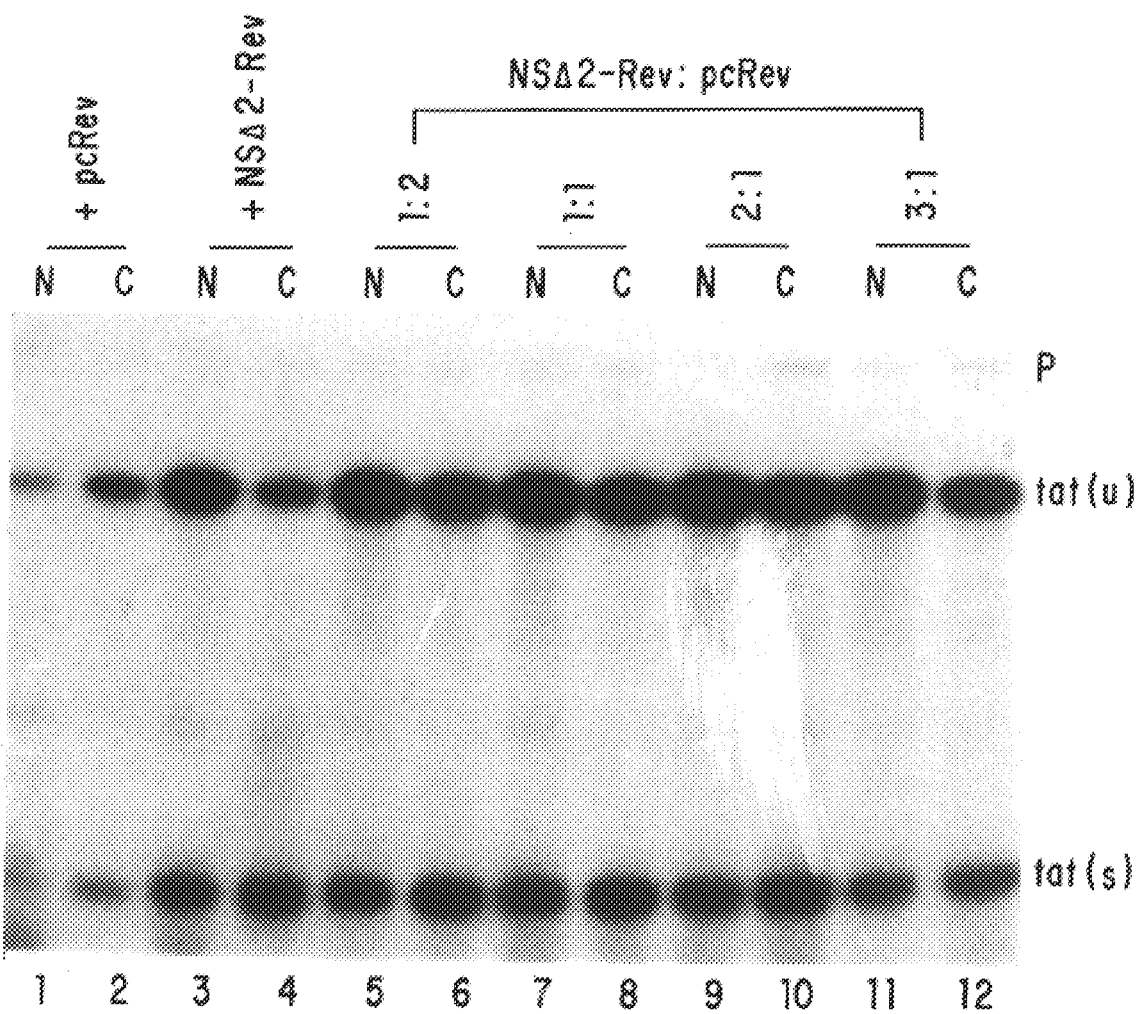

In order to determine whether NSM2 by itself might inhibit the ability of Rev to facilitate unspliced tat mRNA transport, NSM2, pcRev and pgtat plasmids were cotransfected into 293 cells. With increasing NSM2 to pcRev ratio, no obvious reversal effects were observed (FIG. 7). This suggests that the inhibition of Rev function by NSM2-Rev or NSM2-RevM 10 hybrid requires the Rev RNA binding domain.

6.8 Fusion Protein With Peptide Linker

To prepare an NS1 -Rev fusion protein having a peptide linker between the NS1 and Rev portions of, e.g., greater than two residues, the following method is used.

A plasmid segment is assembled essentially as described by Chaudhaury et al., 1989, *Nature* 339:394, except that DNA segments encoding NS1 and Rev proteins are employed. The DNA encoding the linker segment may be ligated by art known methods between the DNA encoding NS1 or a fragment thereof and Rev or a fragment thereof. Peptide linkers of varying length and flexibility are provided, and the resulting chimeric DNA molecules are screened, as described supra, for optimum potency in inhibiting HIV-1 replication in a co-transfection assay.

6.9 Confirmation of Anti-HIV-1 Effect

A full length clone of HIV-1, PNL43, was transfected into 393 cells, alone or with NS3ssdm, NS1, NS1-Rev, NSM2-Rev and NSM2-RevM10 at a 3:1 ratio over the HIV-1. HIV-1 replication was measured by reverse transcriptase activity (RT) over 72 hours. As can be seen in FIG. 10, it is clear that NS1, NS1-Rev and NSM2-Rev have significant anti-HIV-1 replication activity.

6.10 Discussion

HIV-1 is the predominant etiologic agent of the Acquired Immune Deficiency Syndrome (AIDS). The HIV-1 Rev trans-activator has been shown to be essential for viral replication in culture (Terwilliger et al., 1988). Rev binds specifically to RRE (Rev response element) in incompletely spliced HIV-1 transcripts. Binding of Rev permits these nuclear transcripts to be exported to the cytoplasm, where they serve as mRNAs encoding virion structure proteins. Because these essential mRNAs remain confined to the nucleus when Rev is absent, HIV-1 proviruses that lack a functional Rev gene are unable to produce infectious virions (Feinberg et al., 1986; Sadale et al., 1984; Sodroski et al., Terwilliger et al., 1988). This finding suggests that therapies designed to inhibit Rev activity might be of value in treating HIV-1 infections. It has been shown that when present in large excess, the dominant negative mutants in the effector domain of Rev acts as an competitive inhibitor of wild-type Rev directly by forming stable but nonfunctional complexes with the wild-type protein (Hope et al., 1992). The Examples, supra, use transient gene expression analysis in transfected cells to assess the biological activity of Rev protein in the presence of wild-type NS1 protein or various NS1-Rev chimeras. The results suggest that NS1 is dominant over Rev in controlling mRNA transport. While not wishing to be bound by any hypothesis as to how this effect occurs, this effect is at least partially caused by the inhibitory function on Rev mRNA export from the nucleus by NS1 protein, which in turn inhibits the Rev protein expression. Whereas the chimera between an NS1 RNA-binding domain mutant and Rev (NSM2-Rev) or Rev effector domain mutant (NSM2-RevM10) also inhibits Rev function with no apparent inhibition on Rev expression. At a ratio of 2:1 to 3:1 between these chimeras and wild-type Rev, the transport of an RRe-containing viral pre-mRNA (pgtat) is efficiently inhibited. The results also demonstrate that, in order for the hybrid protein to inhibit Rev function, the effector domain of NS1 is required.

Again, without wishing to be bound by a hypothesis as to how the fusion protein operates, it is believed that there are two possible mechanisms involved. First, since these hybrid proteins (NSM2-Rev and NSM2-RevM10) have NS1 effector domain and Rev RNA binding domain, through the direct binding to RRE containing target (pgtat) the effector domain of NS1 presumably interacts with cellular nuclear targets to carry out the function ofinhibiting the nuclear export of RNA target (pgtat). Even with the presence of wild-type Rev protein, increasing amount of hybrid protein can efficiently compete with Rev for its target. Second, the protein presumably can form non- functional heterodimers with wild-type Rev since all those constructs have intact Rev dimerization/RNA-binding domain, with enough amount of hybrid NSM2-Rev or NSM2-RevM 10, most of wild-type Rev can be sequested, which in turn inactivates the wild-type Rev function. It should be noted that there are no definitive evidence yet to demonstrate a complex formation between those NS1-Rev hybrid protein and wild-type Rev protein.

To determine whether the inhibition of Rev function by NSM2-Rev or NSM2-RevM10is solely caused by forming nonfunctional complex with wild-type Rev protein, the following experiment was performed. A plasmid coding for a hybrid protein between NSΔ2 and wild-type Rev, NSΔ2-Rev (FIG. 1), was cotransfected with pcRev plasmid (encoding for wild-type Rev protein) at an increasing NSΔ2-Rev to Rev ratio (FIG. 8). Even at 3:1 ratio between NSΔ2-Rev and Rev, no obvious inhibition of Rev function by this hybrid protein was observed (lanes 11-12). This suggests that the NS1 effector domain is required to overcome the Rev function.

7. Conclusion

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims. Various publications are cited herein, the disclosures of which are incorporated by reference in their entireties.

We claim:

1. A chimeric nucleic acid molecule comprising a coding sequence that encodes a fusion protein comprising an influenza A virus-NS1 protein linked to an HIV-1 Rev protein, wherein said fusion protein inhibits Rev function.

2. The chimeric nucleic acid molecule according to claim 1 wherein said fusion protein comprises wild-type influenza A virus NSI protein linked to wild-type HIV-1-Rev protein.

3. The chimeric nucleic acid molecule according to claim 1 wherein said fusion protein comprises an influenza A virus-NS1 mutant.

4. The chimeric nucleic acid molecule according to claim 1 wherein said fusion protein comprises an HIV-1-Rev protein mutant.

5. The chimeric nucleic acid molecule according to claim 1 wherein said nucleic acid molecule is substantially isolated and purified and is selected from the group consisting of DNA and RNA.

6. An expression vector comprising said nucleic acid molecule according to claim 1.

7. The chimeric nucleic acid molecule according to claim 1 wherein said fusion protein comprises NSM2 linked to Rev, NS linked to RevM5, NSM2 linked to RevM10, NS linked to Rev, NSM3 linked to Rev, NSM3 linked to RevM10, NS(M2+M3) linked to Rev or NS(M2+M3) linked to RevM10.

8. The expression vector according to claim 6 encoding a fusion protein that comprises a wild-type influenza A virus-NS1 protein linked to a wild-type HIV-1-Rev protein.

9. The expression vector according to claim 6 encoding a fusion protein that comprises an influenza A virus-NS1 protein mutant.

10. The expression vector according to claim 6 encoding a fusion protein that comprises an HIV-1-Rev protein mutant.

11. The expression vector according to claim 6 encoding a fusion protein that is expressed under the control of a promoter.

12. A host cell transformed by the vector of claim 6 wherein said host cell is a human lymphocyte.

13. The expression vector according to claim 6 selected from the group consisting of a plasmid and a viral vector.

14. A host cell transformed by the vector of claim 6, wherein said host cell is selected from the group consisting of a prokaryotic host cell and a eukaryotic host cell.

15. The expression vector according to claim 6 wherein said fusion protein comprises NSM2 linked to Rev, NS linked to RevM5, NSM2 linked to RevM10, NS linked to Rev, NSM3 linked to RevM5, NSM3 linked to RevM10, NS(M2+M3) linked to Rev or NS(M2+M3) linked to RevM10.

16. An HIV-Rev influenza A virus-NS1 fusion protein, comprising an influenza A virus-NS1 protein linked to an HIV-1 -Rev protein, wherein said fusion protein inhibits Rev function.

17. The fusion protein according to claims 16 wherein said fusion protein comprises a wild-type influenza A virus-NS1 protein linked to a wild-type HIV-1-Rev protein.

18. The fusion protein according to claim 17 wherein said fusion protein comprises an influenza A virus-NS1 protein mutant.

19. The fusion protein according to claim 17 wherein said fusion protein comprises an HIV-Rev protein mutant.

20. The fusion protein according to claim 17 wherein said fusion protein comprises NSM2 linked to Rev, NS linked to RevM5, NSM2 linked to RevM10, NS linked to Rev, NSM3 linked to Rev, NSM3 linked to RevM10, NS(M2+M3) linked to Rev or NS(M2+M3) linked to RevM10.

21. A composition comprising a nucleic acid vector encoding an HIV-1-Rev, influenza A virus-NS1 fusion protein, said protein having Rev function inhibitory activity and a pharmaceutically acceptable carrier.

22. A composition according to claim 21 wherein said pharmaceutical carrier is selected from the group consisting of a physiological buffer, physiological saline, saline, a slow release carrier, an emulsion and a liposome preparation.

23. A composition comprising an HIV-Rev NS1 fusion protein, said protein having Rev function inhibitory activity and a pharmaceutically acceptable carrier.

24. A composition according to claim 23 wherein said pharmaceutical carrier is selected from the group consisting of a physiological buffer, a slow release carrier, an emulsion and a liposome preparation.

25. A method of producing an HIV-1 Rev, influenza A virus-NS1 fusion protein comprising the steps of:

a. inserting an expression vector comprising a nucleic acid moleule encoding an HIV-1-Rev, influenza A virus-NS1 fusion protein into an isolated host cell; and b. causing siad host cell to express said fusion protein.

26. The method according to claim 25 wherein said host cell is selected from the group consisting of a prokaryotic host cell and a eukaryotic host cell.

27. The method according to claim 26 wherein said eukaryotic host cell is a human lymphocyte.

28. A host cell comprising a chimeric nucleic acid molecule encoding an HIV-1-Rev, influenza A virus-NS1 fusion protein, said protein having Rev function inhibitory activity.

29. The host cell according to claim 28 wherein said fusion protein comprises a wild-type influenza A virus-NS 1 protein linked to a wild-type HIV-1-Rev protein.

30. The host cell according to claim 28 wherein said fusion protein comprises a influenza A virus-NS1 binding domain mutant.

31. The host cell according to claim 28 wherein said fusion protein comprises a Rev protein mutant.

32. The host cell according to claim 28 wherein said fusion protein comprises NSM2 to Rev NS linked to RevM5, NSM2 linked to RevM10NS linked to Rev NSM3 linked to Rev NSM3 linked to RevM10 NS(M2+M3) linked to Rev or NS(M2+M3) linked to RevM10.

33. The host cell according to claim 28 wherein the host cell is selected from the group consisting of a prokaryotic and eukaryotic cell.

34. The host cell according to claim, 29 wherein said chimeric nucleic acid molecule is operably linked to an expression vector.

35. The host cell according to claim 33 wherein the eukaryotic cell is a human lymphocyte.

36. The host cell according to claim 34 wherein said expression vector is selected from the group consisting of a plasmid and a viral vector.

* * * * *